(12) United States Patent
Chrysler et al.

(10) Patent No.: US 6,221,645 B1
(45) Date of Patent: *Apr. 24, 2001

(54) β-SECRETASE ANTIBODY

(75) Inventors: Susanna M. S. Chrysler, San Bruno; Sukanto Sinha, San Francisco; Pamela S. Keim, San Mateo; John P. Anderson, San Francisco; Hua Tan, Daly City; Lisa Clair McConlogue, San Francisco, all of CA (US)

(73) Assignee: Elan Pharmaceuticals, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/660,531

(22) Filed: Jun. 7, 1996

Related U.S. Application Data

(63) Continuation-in-part of application No. 08/480,498, filed on Jun. 7, 1995, now Pat. No. 5,744,346.

(51) Int. Cl.$^7$ .................................................. C07K 16/00
(52) U.S. Cl. ..................... 435/226; 435/212; 435/219; 530/387.1; 530/388.1; 530/388.15; 530/388.26
(58) Field of Search .................... 435/226, 219, 435/212; 530/387.1, 388.26, 388.1, 388.15

(56) References Cited

U.S. PATENT DOCUMENTS 5,424,205   6/1995   Dovey et al. .

FOREIGN PATENT DOCUMENTS

WO 91/13904   9/1991   (WO) .

OTHER PUBLICATIONS

Tagawa et al. "Alzheimer's disease amyloid β–clipping enzyme (APP secretase): Indentification, purification and characterization of the enzyme," *Biochemical and Biophysical Research Communication*, 1991, vol. 177, No. 1, pp. 377–387, especially pp. 379–380.

Sambamurti et al. "Evidence for intracellular cleavage of the Alzheimer's amyloid precursor in PC12 cells," *Journal of Neuroscience Research*, vol. 33, pp. 319–329, entire document.

Nelson et al. "Identification of a Chymotrypsin–Like Mast Cell Protease in Rat Brain Capable of Generating the N–Terminus of the Alzheimer Amyloid β–Protein," *Journal of Neurochemistry*, 1993, vol. 61, No. 2, pp. 567–577, especially pp. 571–572.

Glenner et al. "Advances in Behavioral Biology," *Alzheimer's and Parkinson's Diseases: Recent Developments*, Plenum Press, New York, 1995, vol. 44, pp. 127–130, especially p. 129, third and seventh paragraphs.

Haass et al. "Amyloid β–Peptide is Produced by Cultured Cells During Normal Metabolism," *Nature* 359:322–325 (1992).

Kang et al. "The Precursor of Alzheimer's Disease Amyloid A4 Protein Resembles A Cell–Surface Receptor," *Nature* 325:733–736 (1987).

Selkoe, Dennis J. "Cell Biology of the Amyloid β–Protein Precursor and the Mechanism of Alzheimer's Disease," *Annu. Rev. Cell Biol.* pp. 373–403 (1994).

Seubert et al. "Isolation and Quantification of Soluble Alzheimer's β–Peptide From Biological Fluids," *Nature* 359:325–327 (1992).

*Primary Examiner*—Leon B. Lankford, Jr.

(57) ABSTRACT

Compositions comprising a novel protease capable of cleaving β-amyloid precursor protein (APP) on the amino-terminal side of the β-amyloid peptide therein are provided. The protease is designated β-secretase. Reaction systems comprising β-secretase may be used in screening assays to monitor β-secretase modulated cleavage of APP and to identify β-secretase inhibitors, wherein the β-secretase is in the presence of a suitable polypeptide substrate and cleavage of the substrate determined in the presence and absence of the test substance. Antibodies are raised against peptides of β-secretase. Pharmaceutical compositions and methods comprise compounds identified by screening assays.

5 Claims, 15 Drawing Sheets

FIG._1A

```
                              E  S  L  N  A  T  P  Q  V  A  M  Q  V  L  E  I  H  Y  T  P  S  V  K  I  I  P  S  T  P  F  P  Q  E  G  Q  P
                              TTAATTTGACTTGTGTGAATCCAAAGGAAAACCACTGCCAGAACCTGTGTTTGTGGACAAAGGATGGCCGAGAATTACCAGATCCTGACCGAATGGTTGTGAGTGGTAGG   864
                                                                mature protein                                       peptide 2

L  I  L  T  C  E  S  K  G  K  P  L  P  E  P  V  L  W  T  K  D  G  G  E  L  P  D  D  R  M  V  V  S  G  R
                              GAGCTAAACATTCTTTTCCTGAACAAACGGATAATGGTACATATCGATGTGAAGCAGTGCGAATATGTTCTCATTGTGCATGAT   972
                                 peptide 2                                     mature protein
                                        peptide 3

E  L  N  I  L  F  L  N  K  T  D  N  G  T  Y  R  C  E  A  T  N  T  I  G  Q  S  S  A  E  Y  V  L  I  V  H  D
                              GTTCCCAACACTTTGCTTCCCACTACTATCATCCCCTCCCTTACCACTGCACAGTCCAACATCGTAGCAATAACCAGCCCAACCACATCTGCAACAACCAGC  1080
                                                                mature protein V  P  N  T  L  L  P  T  T  I  I  P  S  L  T  T  A  T  V  T  T  V  A  I  T  T  S  P  T  T  S  A  T  T  S
                              AGCATCAGAGATCCTAATGCTTTGGCTGGCCAGAATGGCCCTGACCATGCTCTCATAGGAGGAATAGTGGCTGTAGTTGTATTTGTCACGCTGTGTTCTATCTTTCTG  1188
                                        mature protein S  I  R  D  P  N  A  L  A  G  Q  N  G  P  D  H  A  L  I  G  G  I  V  A  V  V  V  F  V  T  L  C  S  I  F  L
                              CTTGGTCGATATCTGGCAAGGCATAAAGGAACGTATTTAACAAATGAAGCTAAGAAGCTGACAGCCATTATCAACGCTGAAGGCAGC  1296
                                                                mature protein                            putative transmembrane L  G  R  Y  L  A  R  H  K  G  T  Y  L  T  N  E  A  K  G  A  E  D  A  P  D  A  D  T  A  I  I  N  A  E  G  S
                              CAAGTCAATGCTGAAGAGAAAAAAGAGTATTTCATTTAA   1335
                                 mature protein

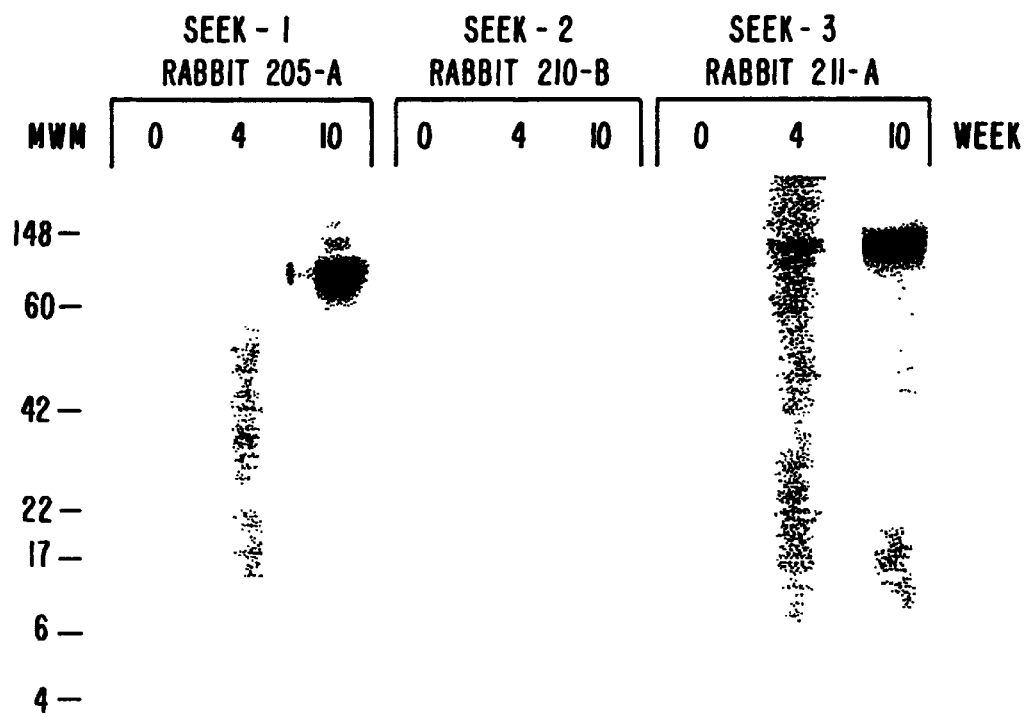
FIG._2
FIG._3

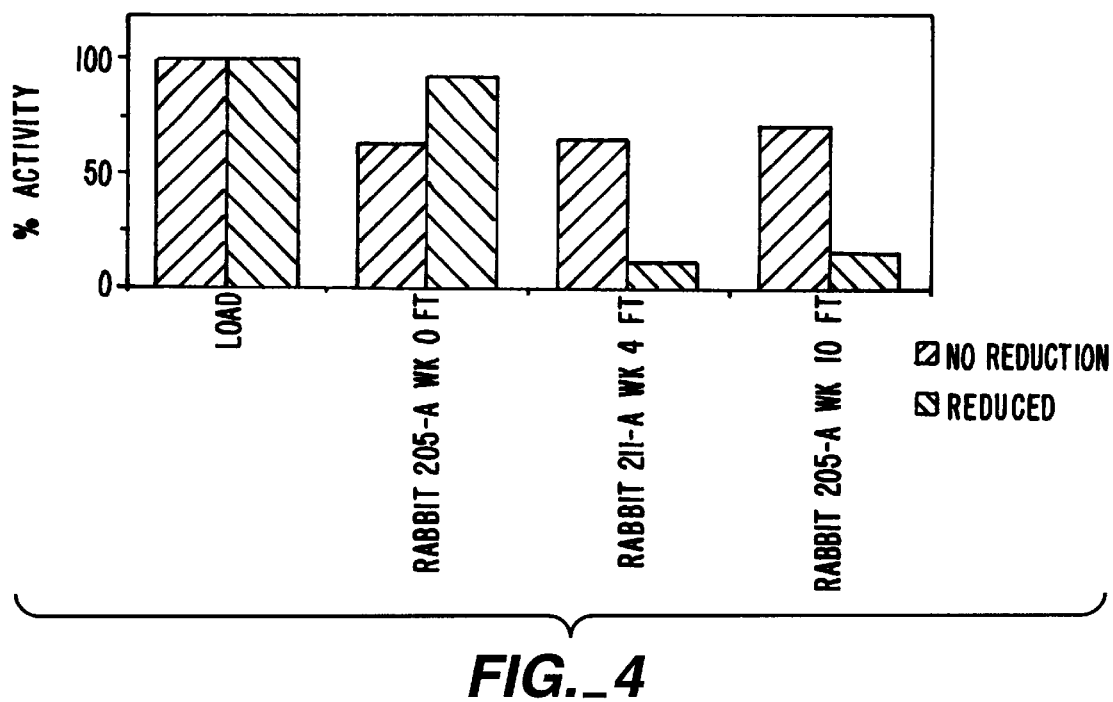
FIG._4
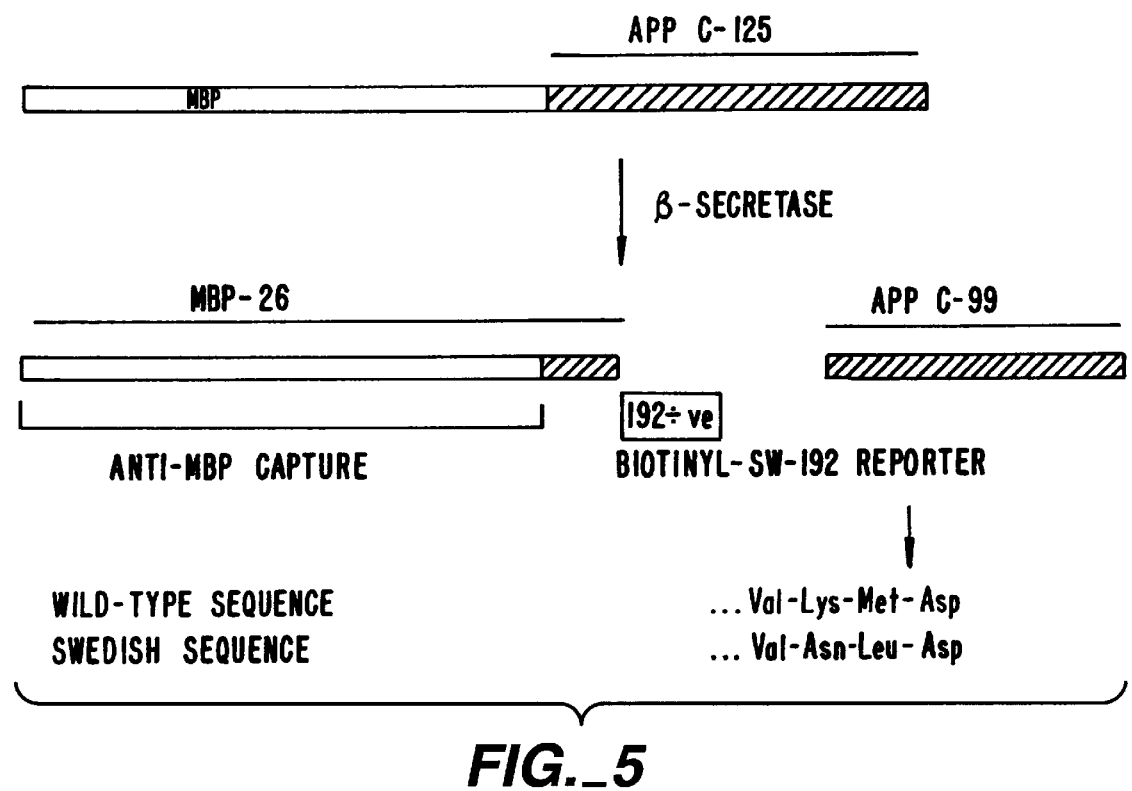
FIG._5

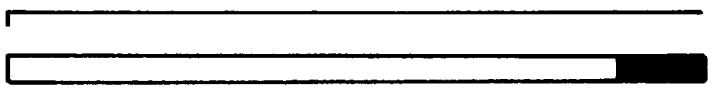
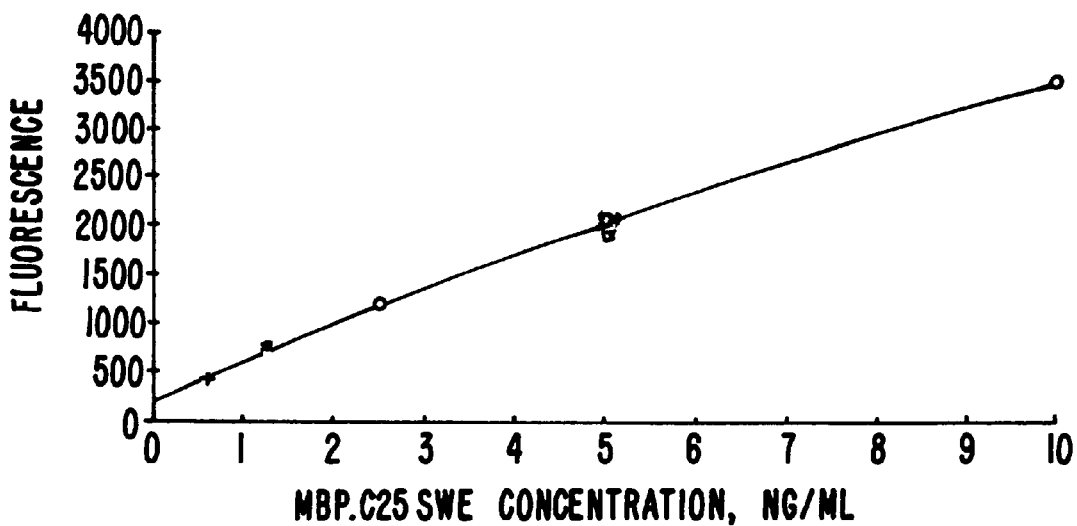
FIG._6
FIG._8

```
  1    ATGAAAACTGAAGAAGGTAAACTGGATTAATCTGGATTAACGGCGATAAAGGCTATAACGGTCTCGCTGAAGTCGGTAAG
  1  ▸ MetLysThrGluGluGlyLysLeuValIleTrpIleAsnGlyAspLysGlyTyrAsnGlyLeuAlaGluValGlyLys

79    AAATTCGAGAAAGATACCGGAATTAAAGTCACCGTTGAGCATCCGTTGAGAAGAAATTCCACAGGTTGCG
 27  ▸ LysPheGluLysAspThrGlyIleLysValThrValGluHisProAspLysLeuGluGluLysPheProGlnValAla

157    GCAACTGGCGATGGCCCTGACATTATCTTCTGGCACACGACCGCTTTGGTGGCCTACGCCGCTTGGCCTGTTGGCT
 53  ▸ AlaThrGlyAspGlyProAspIleIlePheTrpAlaHisAspArgPheGlyGlyTyrAlaGlnSerGlyLeuLeuAla

235    GAAATCACCCCGACAAAGCGTTCCAGGACAAGCGTGTATCCGTTACCTGGGATGCCGTTACAACGGCAAGCTG
 79  ▸ GluIleThrProAspLysArgPheGlnAspLysLeuTyrProPheThrTrpAspAlaValThrArgTyrAsnGlyLysLeu

313    ATTGCTTACCCGATCGCTGTTGAAGCGTTATCGCTGATTTATAACAAAGATCTGCTGCCGAACCCGCCCAAAACCTGG
105  ▸ IleAlaTyrProIleAlaValGluAlaLeuSerLeuIleTyrAsnLysAspLeuLeuProAsnProLysThrTrp

391    GAAGAGATCCCGGCGCTGGATAAAGACCTGCTGATTGCTGCCGAAAGCTAAGGTTATGCGTTCAAGTATGCAAGAACTGCGTG
131  ▸ GluGluIleProAlaLeuAspLysAspLeuLeuIleAlaAlaGluSerLysGlyLeuLysSerAlaLeuMetPheAsnLeuGlnGluProTyr

469    TTCACCTGGCCGCTGATTGCTGCCGCTGGCCGAAAGCGCGGGGTTATGCGTTCAAGTTCGTTGCGTTATGCGTCAAGTAGTGT
157  ▸ PheThrTrpProLeuIleAlaAlaAlaAspProLeuIleAlaAlaPheLysTyrAlaPheLysTyrGluAsnGlyLysLysAspVal

547    GGCGTGCTGAGCGCTGGCCGCCGAAAGCGCGGGTCTGGTTCCCCTGGTTGACCTTCCTGGTTGACCCTGTTCCTGGTTGACCATGCAGAC
183  ▸ GlyValAspAsnAlaGlyAlaAlaGlyAlaLysAsnAlaAlaAspLeuThrPheLeuValAspLeuIleLysAsnLysHisMetAsnAlaAsp

625    ACCGATTACTCCATCGACGAAGCTGCCTTTAATAAAGGCGAAACCAGCAGACGATGACCATCAACGGCCCCGTGGGCATGGTCC
209  ▸ ThrAspTyrSerIleAspGluAlaAlaPheAsnLysGlyGluThrAlaMetThrIleAsnGlyProTrpAlaTrpSer

703    AACATCGACACAGCTGAGCCAGGTTAATTATGGTGTAACGTTGTAACGTTGTTGAGCTGACCTTCAAGGGTCAACCATCCAAACCGTTCGTT
235  ▸ AsnIleAspThrSerLysValAlaAsnTyrGlyValThrValLeuProThrPheLysGlyGlnProSerLysProPheVal

781    GGCGTGCTGAGCGCTGGAAGCTGAAACGGTTAATAAACGCCGGTTAATAAACGCCGAACAAAGAGTTCCTCGAAAAACTATCTGCTG
261  ▸ GlyValLeuSerAlaGlyLysLeuGluAlaLysLysIleAsnAlaAlaSerProAsnLysGluLeuAlaLysGluPheLeuGluAsnTyrLeuLeu

859    ACTGATGAAGGTCTGGAAGCGGTTAATAAAGACAAACCGCTGGGTCTGGCTAGCGCTGAAGTCTTACGAGGAAGAGTTG
287  ▸ ThrAspGluGlyLeuGluAlaValAsnLysAspLysProLeuGlyAlaAlaLeuAlaLeuLysSerTyrGluGluLeuLeu
```

*FIG._7A*

```
 937        GCGAAAGATCCACGTATTGCCGCCACCATGGAAAATCATGCCGAACATCCCGCAGATGTCC
 313      ► AlaLysAspProArgIleAlaAlaThrMetGluAsnAlaGlnLysGlyGluIleMetProGlnMetSer

1015        GCTTTCTGGTATGCCGTGCTACTGCGGTCGATCAACGCCGCCAGCGGTCGTCAGACTGTCGATGAAGCCCTGAAAGAC
 339      ► AlaPheTrpTyrAlaValArgThrAlaValIleAsnAlaAlaSerGlyArgGlnThrValAspGluAlaLeuLysAsp

1093        GCGCAGACTAATTCGAGCTCGGTACCCGGTACCCGGGATCCATCGAGGGTAGGGCCGAGGACCGACCACTCGACCA
 365      ► AlaGlnThrAsnSerSerSerValProGlyArgGlySerIleGluGlyArgGlyArgAlaAspArgGlyLeuThrThrArgPro

1171        GGTTCTGGGTTGACAAATATCAAGACGGAGAGATCTCTGAAGTGAATCTGGATGCAGAATTCCGACATGACTCAGGA
 391      ► GlySerGlyLeuThrAsnIleLysThrGluIleSerGluValAsnLeuAspAlaGluPheArgHisAspSerGly

1249        TATGAAGTTCATCATCAAAAATTGGTGTGTTCTTTGCAGAAGATGTGGGTTCAAACAAAGGTGCAATCATTGGACTCATG
 417      ► TyrGluValHisHisGlnLysLeuValPhePheAlaGluAspValGlySerAsnLysGlyAlaIleIleGlyLeuMet

1327        GTGGGCGGTGTGTTGTCATAGCGACAGTGATCGTCATAGCAGTAGTAGTACACATCCATTCAT
 443      ► ValGlyValValLeuValIleAlaThrValIleValIleThrLeuValMetLeuLysLysGlnTyrThrSerIleHis

1405        CATGGTGTGGTGGAGGTTGACGCGCCGGTTGACGCGCCAGGAGGCGCCACCTGTCCAAGATGCAGCAGAACGGCTACGAA
 469      ► HisGlyValValGluValAspAlaAlaValThrProGluGlyArgHisLeuSerLysMetGlnGlnAsnGlyTyrGlu

1483        AATCCAACCTACAAGTTCTTTGAGCAGATGCAGAACTAG
 495      ► AsnProThrTyrLysPhePheGluGlnMetGlnAsn...
```

*FIG._7B*

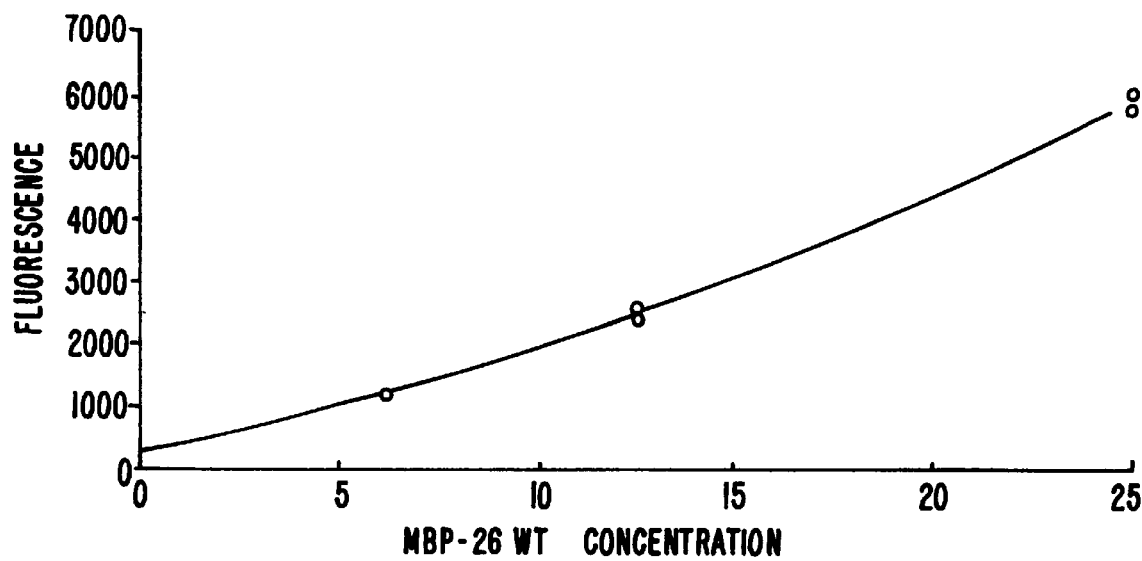
FIG._9
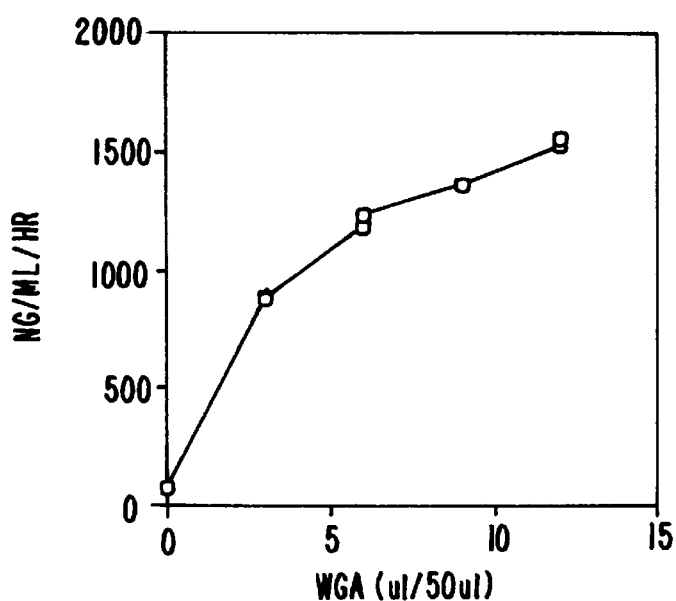
FIG._10

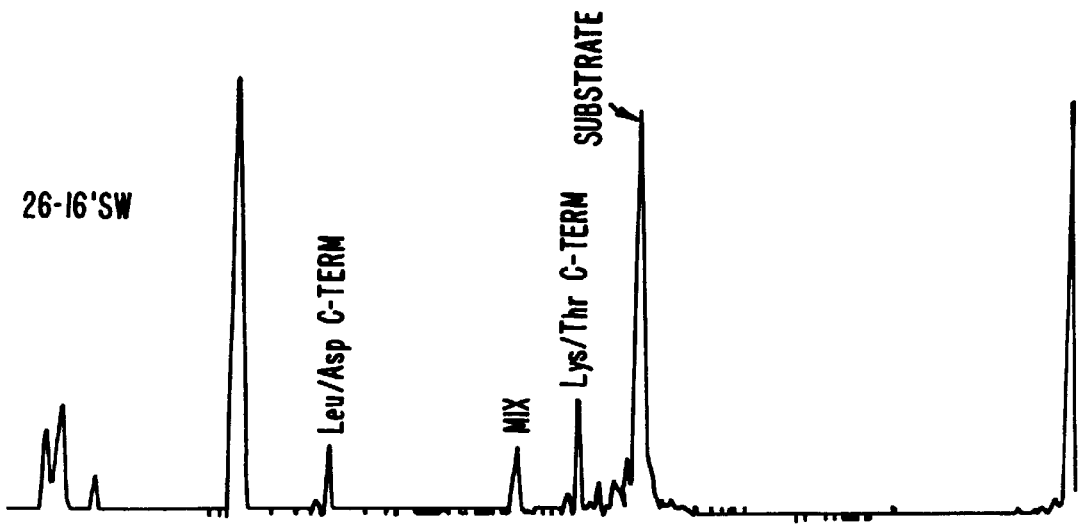
FIG._11A
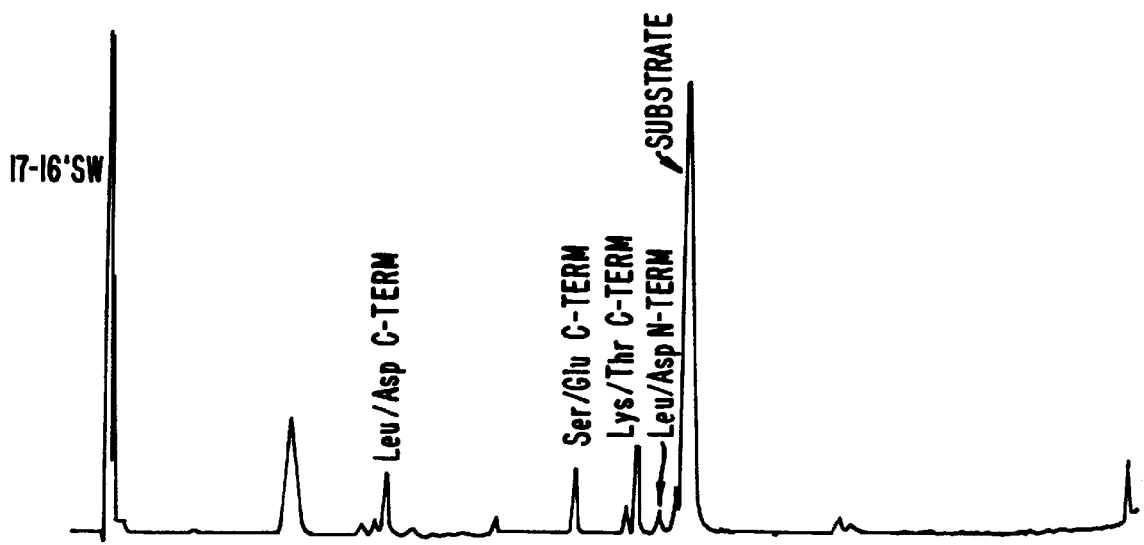
FIG._11B

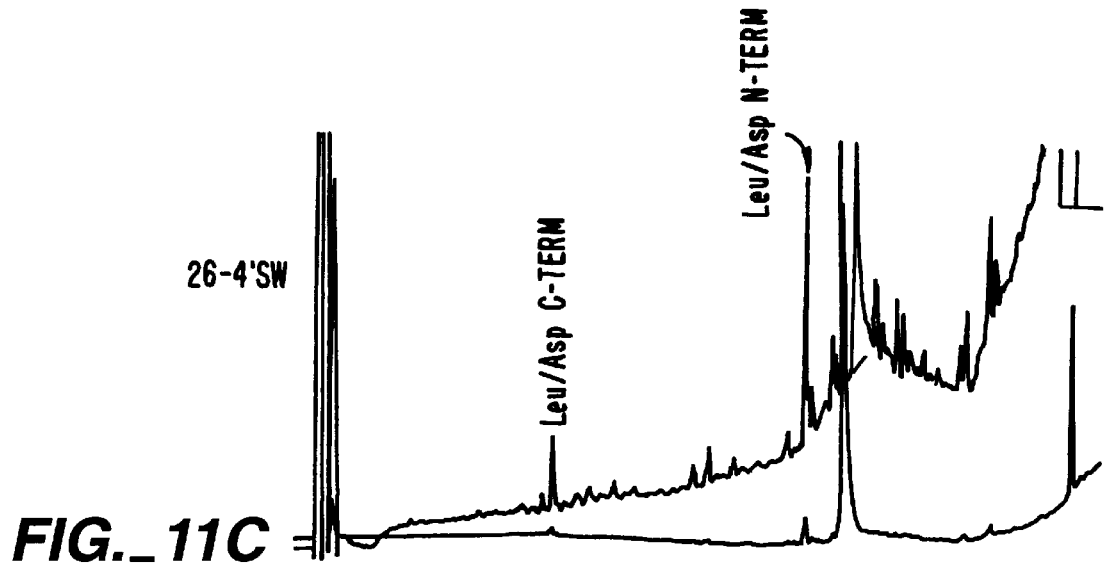
FIG._11C
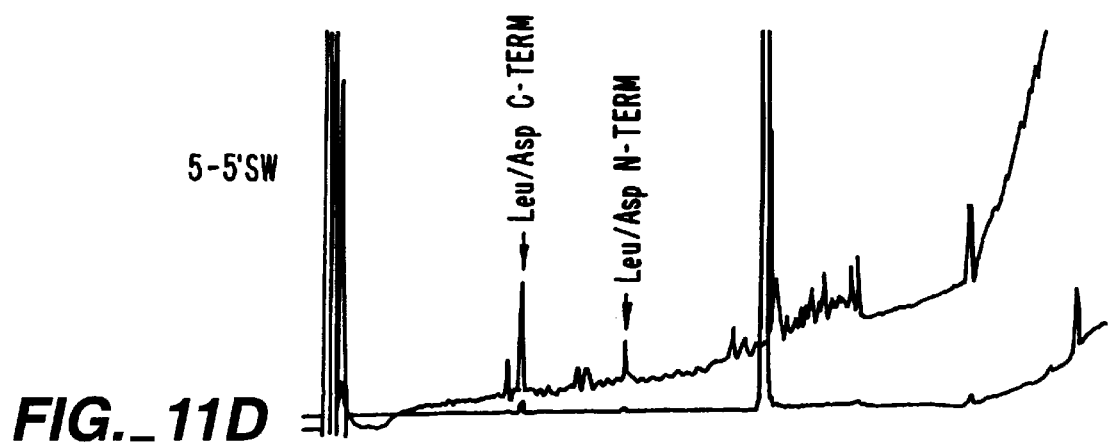
FIG._11D
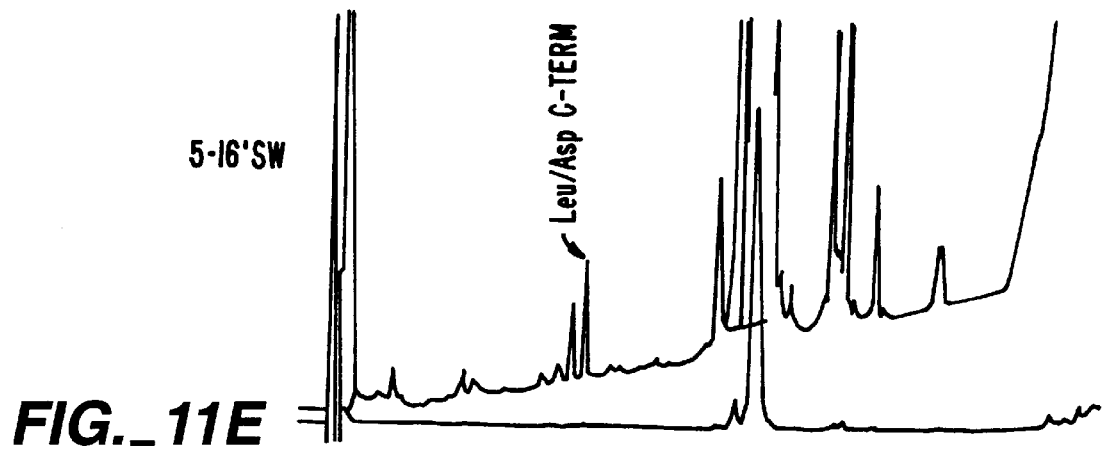
FIG._11E

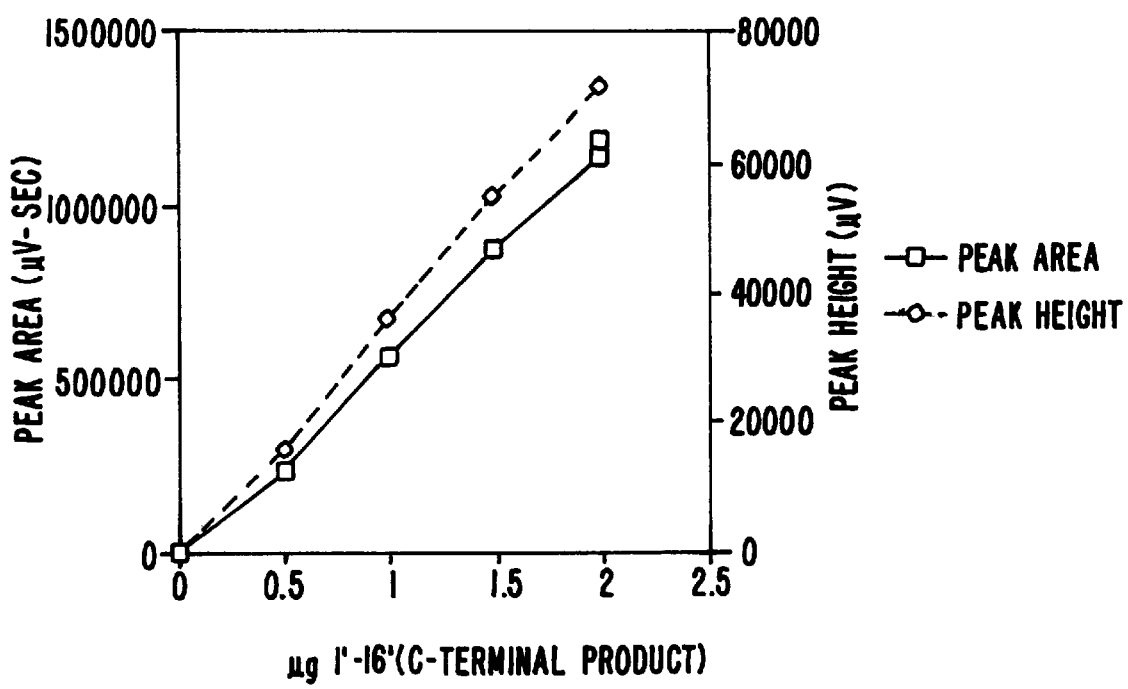
FIG._11F
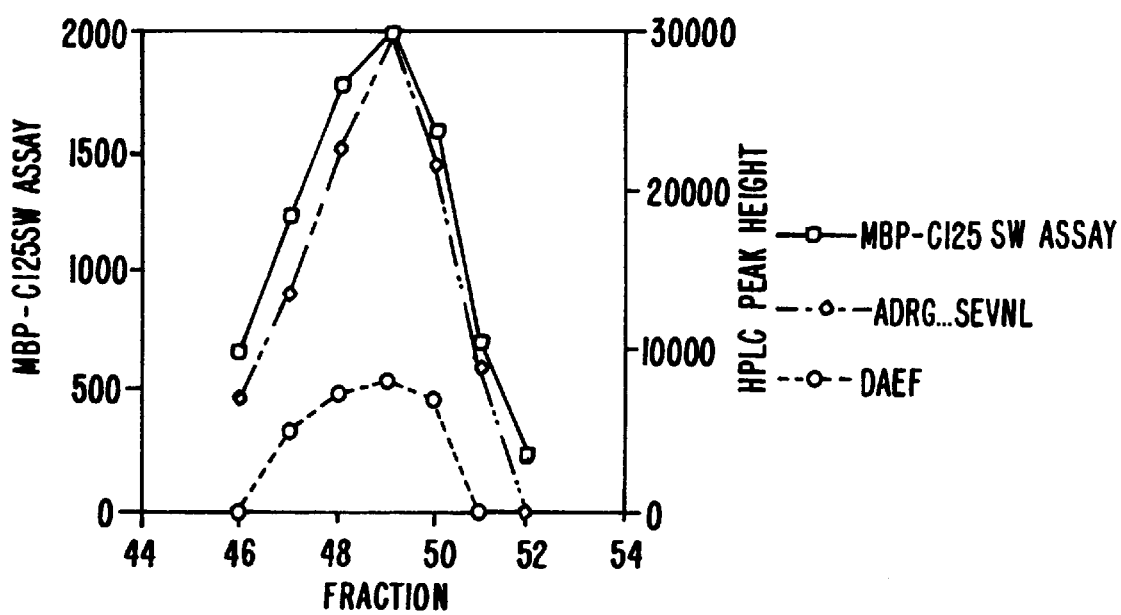
FIG._12A

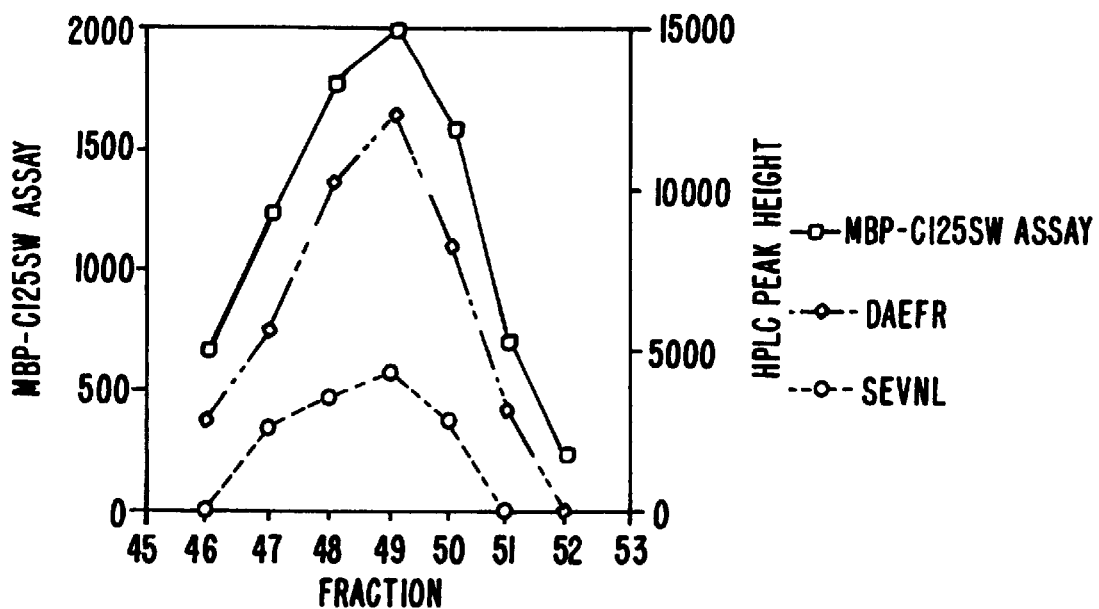
FIG._12B
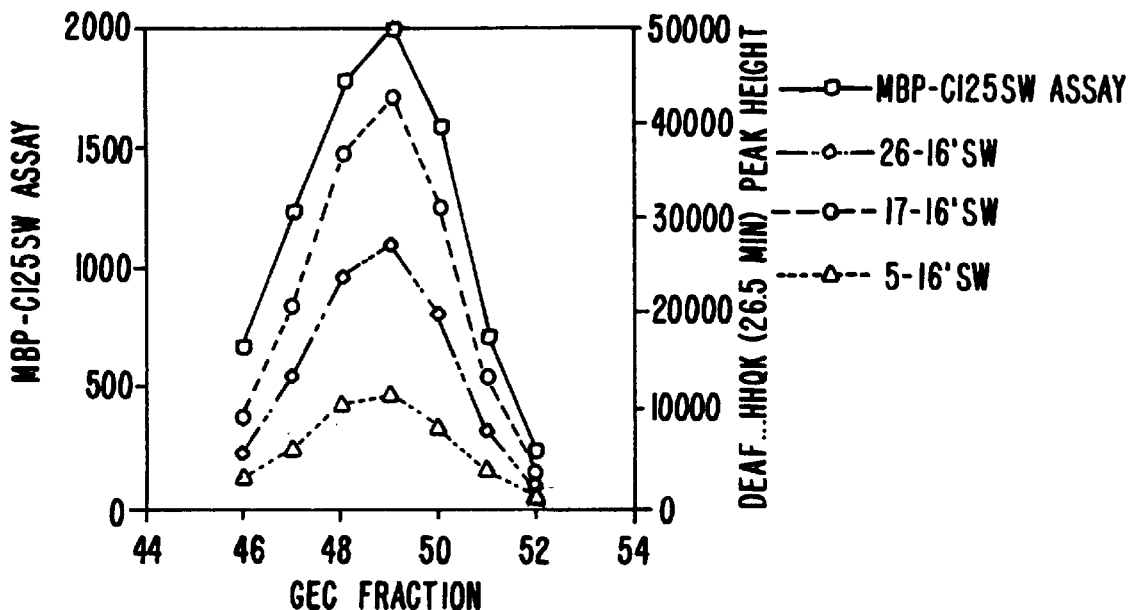
FIG._12C

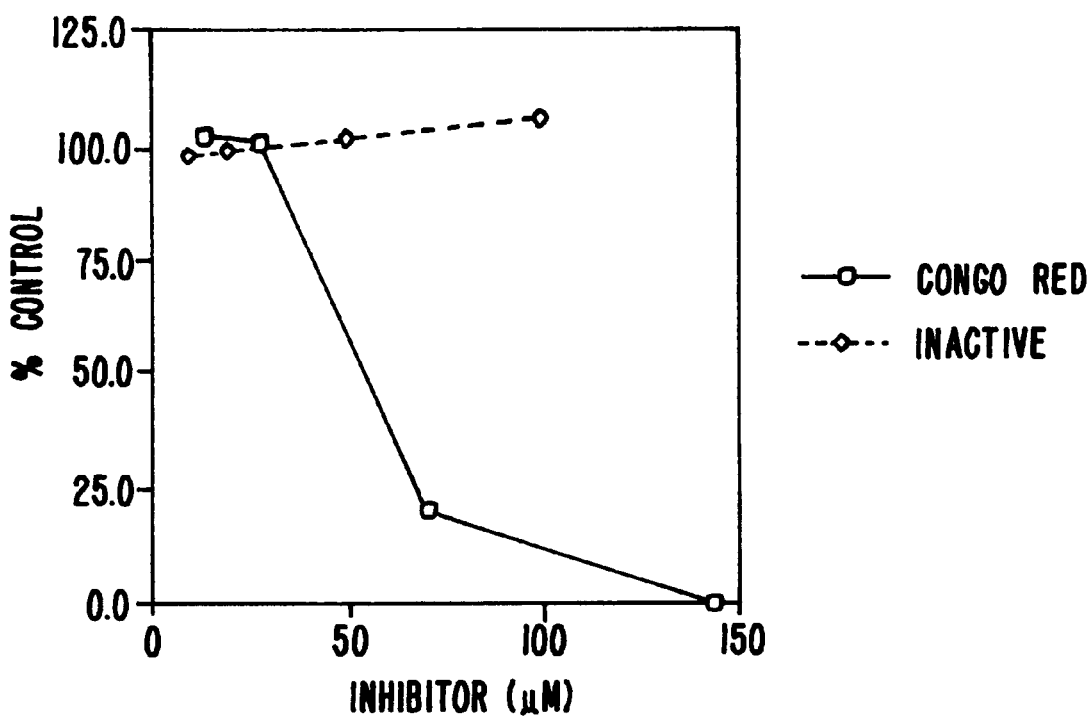
FIG._13
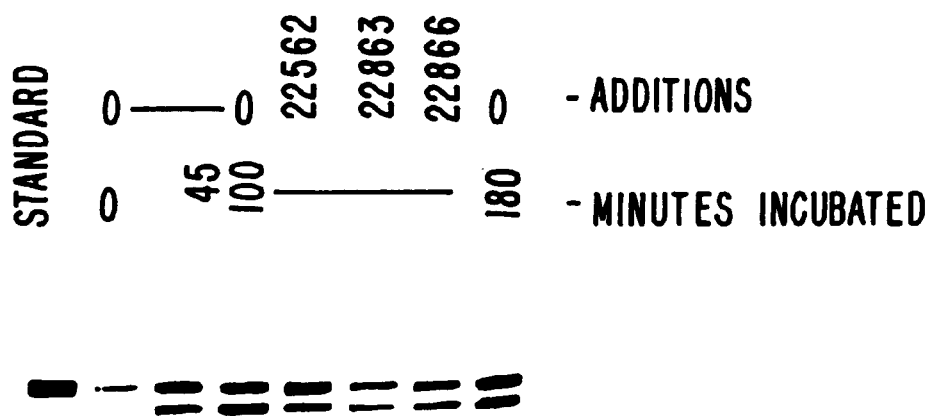
FIG._14

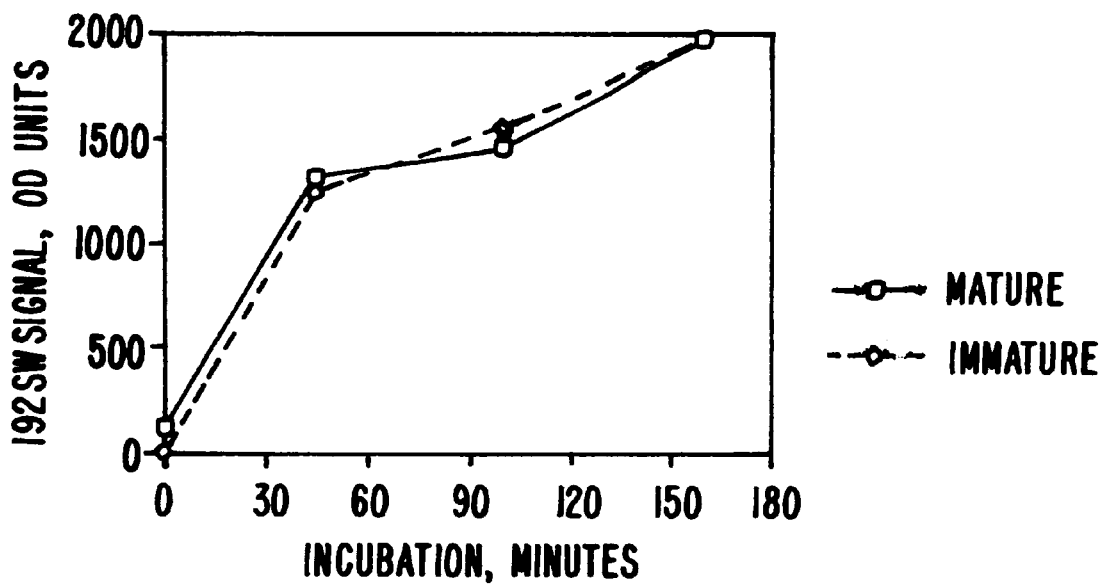
FIG._15
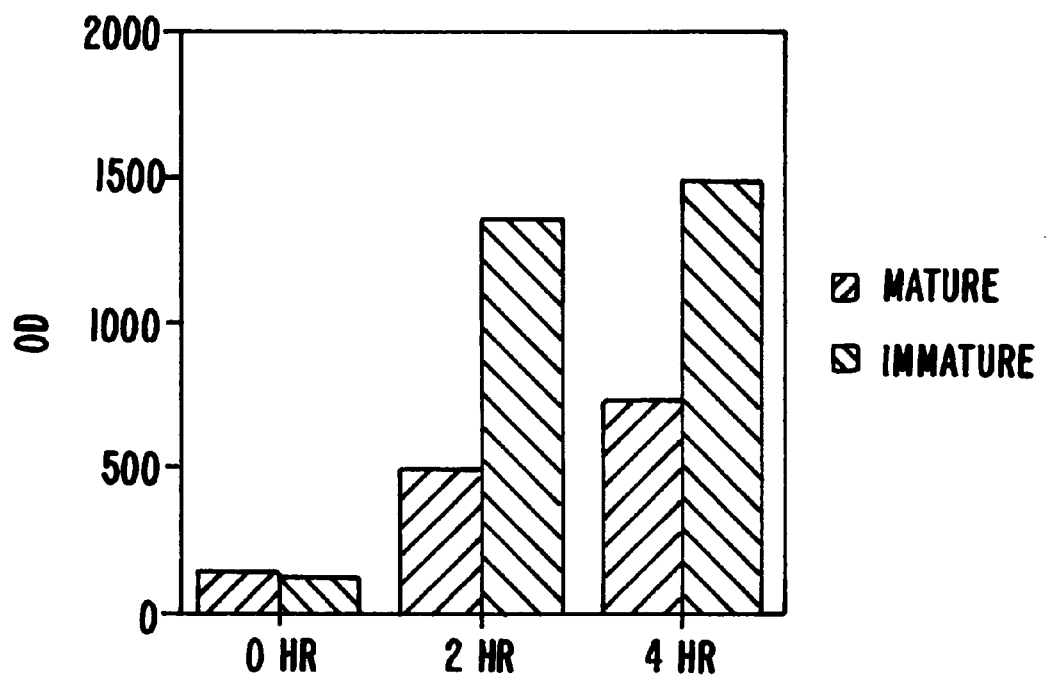
FIG._16

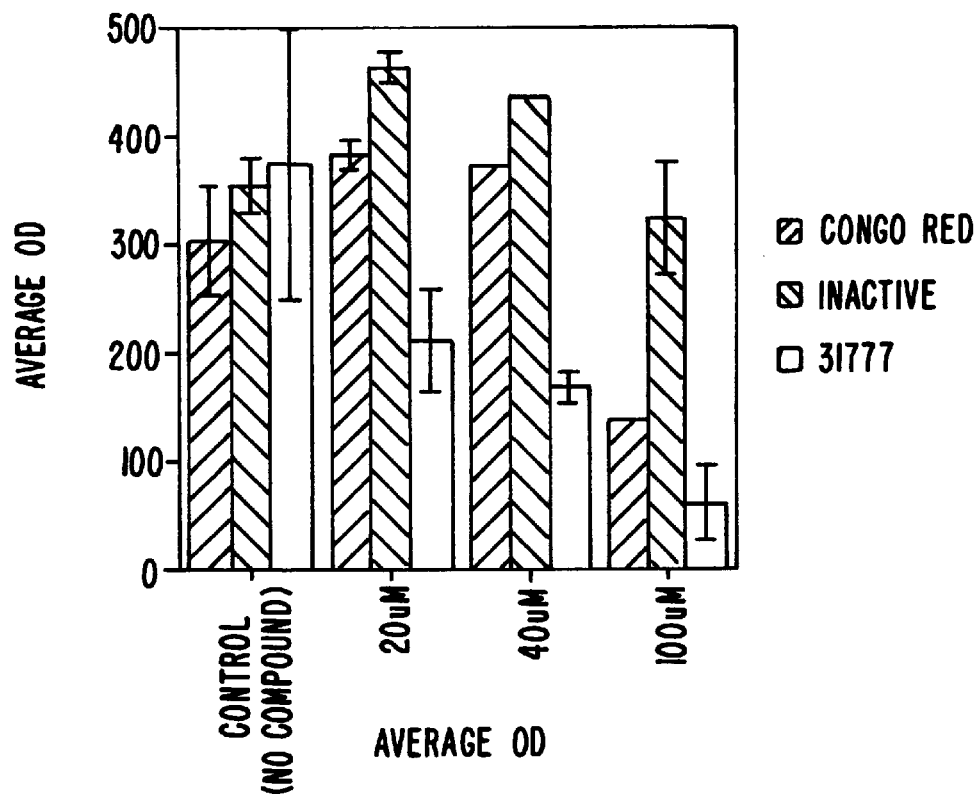
FIG._17
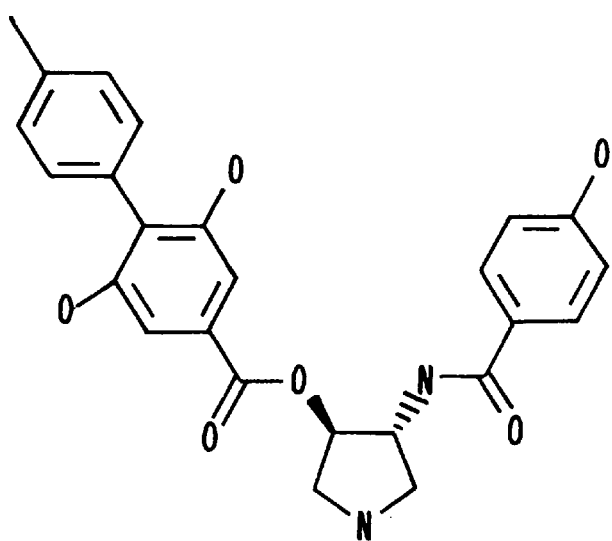
FIG._18

β-SECRETASE ANTIBODY

The present application is a continuation-in-part of application Ser. No. 08/480,498, filed on Jun. 7, 1995 now U.S. Pat. No. 5,744,346. The disclosure of the present application is also related to copending application Ser. Nos. 08/485,152, filed on Jun. 7, 1995 now abandoned, filed on the same day as the present application, both of which are assigned to the assignee of the present application. The full disclosures of each of these three applications are incorporated herein by reference.

BACKGROUND OF THE INVENTION

1. Field of the Invention

The present invention relates generally to the cleavage of β-amyloid precursor protein to produce β-amyloid peptide. More particularly, the present invention relates to isolated and purified compositions containing an enzyme responsible for such cleavage (β-secretase) and assays for identifying inhibitors of β-secretase.

Alzheimer's disease is characterized by the presence of numerous amyloid plaques and neurofibrillary tangles (highly insoluble protein aggregates) present in the brains of Alzheimer's disease patients, particularly in those regions involved with memory and cognition. β-amyloid peptide is a major constituent of amyloid plaque which is produced by cleavage of β-amyloid precursor protein. It is presently believed that a normal (non-pathogenic) processing of the β-amyloid precursor protein occurs via cleavage by a putative "α-secretase" which cleaves between amino acids 16 and 17 of the β-amyloid peptide region within the protein. It is further believed that pathogenic processing occurs in part via a putative "β-secretase" which cleaves at the amino-terminus of the β-amyloid peptide region within the precursor protein. Heretofore, however, the existence of β-secretase has not been confirmed.

The identification, isolation, and characterization of novel biological molecules having unique activities is generally useful. For example, novel enzymes can be used to catalyze reactions of a type associated with their class. In particular, novel proteases can be used to cleave proteins for a variety of purposes, and the availability of new proteases provides unique capabilities. In addition to such uses associated with enzymes in general, the identification, isolation, and purification of the putative β-secretase enzyme would permit chemical modeling of a critical event in the pathology of Alzheimer's disease and would allow the screening of compounds to determine their ability to inhibit β-secretase activity.

For these reasons, it would be desirable to isolate, purify, and characterize the enzyme responsible for the pathogenic cleavage of β-amyloid precursor protein at the amino-terminus of the β-amyloid peptide region. In particular, it would be desirable to utilize such an enzyme (referred to hereinafter as β-secretase) in methods for screening candidate drugs for the ability to inhibit the activity of β-secretase in in vitro systems. It would be particularly desirable if such screening assays could be performed in a rapid format which would permit the screening of large numbers of test drugs in automated fashion.

2. Description of the Background Art

β-amyloid precursor protein (APP) is expressed in three differently-spliced forms of 695, 751, and 770 amino acids, and "normal" processing involves proteolytic cleavage at a site between residues $Lys^{16}$ and $Leu^{17}$ in the β-amyloid peptide. Kang et al. (1987) *Nature* 325:773–776. Soluble β-amyloid peptide which has been cleaved at the putative β-secretase site has also been found in the culture medium of non-diseased cells (Haass et al. (1992) *Nature* 359:322–325) and in CSF from healthy humans and animals (Seubert et al. (1992) *Nature* 359:325–327). The possible existence of the putative β-secretase is discussed in, for example, Selkoe, "Cell Biology of the Amyloid β-Protein and the Mechanism of Alzheimer's Disease," in *Annual Review of Cell Biology*, Spudich et al., eds., Annual Review, Inc., Palo Alto, Calif., vol. 10, 1994. The Swedish mutation of APP is also discussed in Selkoe, supra. See also, Esch et al. (1994) *Science* 248:1122.

SUMMARY OF THE INVENTION

The present invention provides novel β-secretase compositions comprising an isolated and purified enzyme which cleaves β-amyloid precursor protein (APP) at the amino-terminus of β-amyloid peptide (βAP) within APP, referred to hereinafter as "β-secretase activity." The compositions of the present invention will generally have a β-secretase activity which is at least five-fold greater than that of a solubilized but unenriched membrane fraction from human 293 cells, preferably being at least ten-fold greater than that of the membrane fraction, and more preferably being at least 100-fold greater than that of the membrane fraction. The β-secretase enzyme is characterized by (1) an apparent molecular weight in the range from 260 kD to 300 kD as determined by gel exclusion chromatography, (2) a more accurate apparent molecular weight in the range from 60 kD to 148 kD determined by electrophoresis, (3) a net negative charge at pH 5 and a net negative charge at pH 7.5, and (4) binding to wheat germ agglutinin.

The compositions of the present invention are generally useful as proteolytic chemicals and specifically useful in assays for determining whether a test substance will inhibit proteolytic cleavage of APP resulting from the novel β-secretase. The method comprises exposing a polypeptide comprising the β-secretase site of APP (located at the amino-terminus of the βAP region within APP) to an at least partially purified β-secretase in the presence of the test substance under conditions such that the β-secretase would be expected to cleave the polypeptide into an amino-terminal fragment and a carboxy-terminal fragment in the absence of test substance which inhibits such cleavage. Test substances which inhibit such cleavage are thus identified as having β-secretase inhibition activity. Such test methods preferably employ the β-secretase compositions described above. Generation of fragments of APP-derived polypeptides is detected, e.g. by an antibody specific for the carboxy end of the amino terminal fragment or the amino end of the carboxy-terminal fragment. The polypeptide substrate for the β-secretase may comprise a fusion polypeptide including an amino-terminal portion having a binding epitope. Use of such a fusion polypeptide as the β-secretase substrate facilitates detection of cleavage by capture of the amino-terminal portion and labelling of the amino-terminal portion.

The compositions of the present invention further comprise purified β-secretase protein having an amino acid sequence substantially identical to at least a portion of the amino acid sequence of [SEQ ID No.:1]. Compositions still further comprise β-secretase protein analogs whose amino acid sequence is not naturally occurring or which is a fragment which comprise a contiguous sequence of at least ten amino acids from the amino acid sequence of native β-secretase [SEQ ID No.:1]. In one embodiment, the β-secretase analog or fragment, when presented as an immunogen, elicits the production of an antibody which specifically binds to natural β-secretase protein. In another embodiment, the β-secretase cleaves β-amyloid precursor protein at the β-amyloid peptide cleavage location.

The present invention still further provides recombinant nucleic acid molecules and compositions comprising a nucleotide sequence of at least 25 contiguous nucleotides from [SEQ ID No.:2]. In one embodiment, the recombinant nucleic acid molecule further comprises expression control sequences operatively linked to a nucleic acid sequence which encodes for the expression of a polypeptide whose amino acid sequence comprises a contiguous sequence of at least ten amino acids from [SEQ ID No.:1]. In another aspect, the recombinant nucleic acid molecules are transfected or otherwise introduced to recombinant host cells with an expression vector comprising the recombinant nucleic acid molecule having expression control sequences which provide for expression of β-secretase or a portion thereof having at least ten contiguous amino acids from [SEQ ID No.:1]. The recombinant nucleic acid molecules may further be provided as nucleic acid probes, typically including at least 15 contiguous nucleotides which specifically hybridize to a unique nucleotide sequence of native β-secretase DNA of [SEQ ID No.:2] or with its complement.

The present invention still further provides antibodies and antibody compositions that specifically bind to β-secretase protein. The antibodies may be polycolonal or monocolonal, and may be prepared by immunization of a suitable host with any of the immunogenic β-secretase compositions described above. The antibodies may further be prepared recombinantly, may be humanized, or otherwise modified or produced in accordance with conventional methods for antibody production.

BRIEF DESCRIPTION OF THE DRAWINGS

FIG. 1A and FIG. 1B are the cDNA sequence [SEQ ID No.:4] and deduced amino acid sequence [SEQ ID No.:5] of cloned β-secretase including putative signal peptide. Peptide 1 [SEQ ID No.:6], peptide 2 [SEQ ID No.:7], and peptide 3 [SEQ ID No.:8], are shown as is the putative transmembrane region.

FIG. 2 is a Western blot showing the reactivity of antibodies raised against peptides Seek-1 [SEQ ID No.:9], Seek-2 [SEQ ID No.:10], and Seek-3 [SEQ ID No.:11], under non-reducing conditions, as described in the Experimental section.

FIG. 3 is a similar Western blot to FIG. 9, except that the protein samples were reduced prior to electrophoresis.

FIG. 4 is a chart comparing the immunoprecipitation of β-secretase using the antibodies of FIGS. 9 and 10 under reducing and non-reducing conditions.

FIG. 5 is a schematic illustration of an APP-containing fusion peptide useful as substrates in performing the screening assays of the present invention, having a binding epitope derived from maltose-binding protein (MBP). An assay was run by exposing the fusion polypeptide to β-secretase which cleaves the 125 amino acid portion of APP (APP C-125) at the amino-terminus of the βAP. The MBP portion may then be captured, and the carboxy-terminus of the APP fragment which is exposed by cleavage with β-secretase may be identified with 192 antibody specific for said terminus. SW-192 antibody bound to a reporter is utilized, which antibody recognizes the carboxy-terminus of the Swedish mutation of APP.

FIG. 6 illustrates APP 638 which is a recombinantly expressed form of APP truncated after βAP (Aβ). APP 638 may be used in a β-secretase assay where the βAP peptide is cleaved and the carboxy-terminus of the amino-terminal fragment of APP 638 recognized by 192 antibody in either a Western blot or ELISA assay. The carboxy terminal βAP fragment can also be measured using a 3D6/266 assay.

FIG. 7A and FIG. 7B are the complete nucleotide and amino acid sequence of the Swedish mutation of the fusion polypeptide of maltose-binding protein and APP fragment utilized in the Experimental section hereinafter [SEQ ID No.:3 and SEQ ID No.:21].

FIG. 8 is a standard curve generated for the β-secretase ELISA described in detail in the Experimental section below.

FIG. 9 is a standard curve for a β-secretase assay.

FIG. 10 show the results of a β-secretase assay using the curve of FIG. 9.

FIGS. 11A, 11B, 11C, 11D, 11E and 11F are HPLC analyses of five β-secretase substrate peptides. Labels describe the indicated peptide, e.g. "Leu/Asp C-Term" denotes the C-terminal fragment of cleavage between Leu and Asp. In FIGS. 11C–E, upper trace is the same as the lower trace, but magnified.

FIGS. 12A, 12B, and 12C are summaries of β-secretase activity of GEC fractions, as measured by both peptide cleavage and ELISA assays.

FIG. 13 illustrates the results of a β-secretase inhibition assay using two test compounds (Congo Red and an inactive compound).

FIG. 14 is an autoradiogram showing the detection of β-secretase cleavage products in a cell membrane assay format.

FIG. 15 is a graph illustrating the extent of β-secretase cleavage of mature and immature APP over time.

FIG. 16 is a chart illustrating the extent of β-secretase cleavage of mature and immature APP over more extended time periods.

FIG. 17 illustrates the effect of putative β-secretase inhibitors of β-secretase cleavage of APP in the cell membrane assay.

FIG. 18 is a structural formula of a compound tested by the inhibition assay of the present invention, as described in the Experimental section below.

DESCRIPTION OF THE PREFERRED EMBODIMENT

The present invention provides a novel protease which specifically cleaves the β-amyloid precursor protein (APP) at the amino-terminus of the β-amyloid peptide (βAP) therein. It is believed that this protease is the putative β-secretase responsible for the pathogenic processing of APP to produce βAP in βAP-related conditions, such as Alzheimer's disease, Down's syndrome, HCHWA-D, and the like. Thus, the novel protease of the present invention will be referred to hereinafter as "β-secretase." The β-secretase of the present invention will be useful as a protease in in vitro and in vivo systems where proteases may generally find use. For example, β-secretase may be used to cleave or attempt to cleave proteins in order to characterize, process, modify, or otherwise react with the protein as a substrate. Thus, β-secretase will have general utility as a proteolytic chemical reagent in a wide variety of chemical reactions and systems. In addition, the β-secretase of the present invention will have a specific utility in the performance of screening assays to identify β-secretase inhibitors, i.e., test compounds which are able to inhibit the proteolytic cleavage of APP in the presence of β-secretase. Such assays will be described in detail below. In addition to the β-secretase compositions and screening assay methods, the present invention will further provide recombinant nucleic acid molecules which encode at least a portion of β-secretase and which are useful for a variety of purposes, including expression of β-secretase, detection of β-secretase genes, and the like. The present invention will still further provide recombinantly produced β-secretase molecules and compositions, usually by the expression of all or a portion of the β-secretase gene. The present invention will still further provide antibodies to epitopes on the native β-secretase protein which are useful for screening and other assays.

1. DEFINITIONS

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, "β-amyloid precursor protein" (APP) refers to a polypeptide that is encoded by a gene of the same name localized in humans on the long arm of chromosome 21 and that includes a βAP region (defined below) within its carboxyl third. APP is a glycosylated, single-membrane-spanning protein expressed in a wide variety of cells in many mammalian tissues. Examples of specific isotypes of APP which are currently known to exist in humans are the 695-amino acid polypeptide described by Kang et al. (1987) Nature 325:733–736. A 751-amino acid polypeptide has been described by Ponte et al. (1988) Nature 331:525–527 and Tanzi et al. (1988) Nature 331:528–530. A 770-amino acid isotype of APP is described in Kitaguchi et al. (1988) Nature 331:530–532. A number of specific variants of APP have also been described having point mutations which can differ in both position and phenotype. A general review of such mutations is provided in Hardy (1992) Nature Genet. 1:233–234. A mutation of particular interest is designated the "Swedish" mutation where the normal Lys-Met residues at positions 595 and 596 of the 695 form are replaced by Asn-Leu. This mutation is located directly upstream of the normal β-secretase cleavage site of APP, which occurs between residues 596 and 597 of the 695 form.

As used herein, "β-amyloid peptide" (βAP) refers to a family of peptides having lengths from 28 to 43 amino acids, with a common 43 amino acid form comprising residues 597–640 of the 695 amino acid isotype of APP. BAP is produced by processing of the APP including cleavage at both the amino-terminus and carboxy-terminus of the region. It is believed that the β-secretase of the present invention is responsible for cleavage of APP at the amino-terminus of βAP in normal and pathogenic processing of APP in human cells.

As used herein, "specifically cleaves β-amyloid precursor protein (APP) at the β-amyloid peptide cleavage location" means that the β-secretase cleaves APP at only a single location and only at the site between amino acids 596 and 597 of the 695 isotype. Test for determining whether an enzyme possesses such specificity are described in the Experimental section hereinafter under the headings β-secretase Inhibitor Assays, Assays utilizing purified β-secretase and recombinant fusion peptide substrates. β-secretase will cleave the MBP-C125 SW substrate at only the β-cleavage site and no other locations.

The term "nucleic acid" refers to a deoxyribonucleotide or ribonucleotide polymer in either single- or double-stranded form, and, unless otherwise limited, encompasses known analogs of natural nucleotides that can function in a similar manner as naturally occurring nucleotides. It will be understood that when a nucleic acid molecule is said to have a DNA sequence, this also includes RNA molecules having the corresponding RNA sequence in which "U" replaces "T".

The term "recombinant nucleic acid molecule" refers to a nucleic acid molecule which is not naturally occurring, and which comprises two nucleotide sequences which are not naturally joined together. Recombinant nucleic acid molecules are produced by artificial recombination, e.g., genetic engineering techniques or chemical synthesis.

The term "coding for expression of" a polypeptide, when used in reference to a nucleotide sequence, refers to a sequence that, upon transcription and translation of mRNA, produces the polypeptide. As any person skilled in the art recognizes, this includes all degenerate nucleotide sequences encoding the amino acid sequence. This can include sequences containing, e.g., introns.

As used herein, the term "expression control sequences" refers to nucleotide sequences that regulate the expression of a nucleotide sequence to which they are operatively linked. Expression control sequences are "operatively linked" to a nucleotide sequence when the expression control sequences control and regulate the transcription and, as appropriate, translation of the nucleotide sequence. Thus, expression control sequences can include appropriate promoters, enhancers, transcription terminators, a start condon (i.e., ATG) in front of a protein-encoding gene, splicing signals for introns, maintenance of the correct reading frame of that gene to permit proper translation of the mRNA, and stop codons.

The term "nucleic acid probe" refers to a nucleic acid molecule which binds to a specific sequence or sub-sequence of another nucleic acid molecule. A probe is preferably a nucleic acid molecule which binds through complementary base pairing to the full sequence or to a sub-sequence of a target nucleic acid. It will be understood by a person skilled in the art that probes may bind target sequences lacking complete complementarity with the probable sequence depending upon the stringency of the hybridization conditions. The probes are preferably directly labelled as with isotopes, chromophores, lumiphores, chromogens, or indirectly labelled such as with biotin to which a streptavidin complex may later bind. By assaying for the presence or absence of the probe, one can detect the presence or absence of the select sequence or sub-sequence.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "recombinant protein" and "recombinant β-secretase" refer to a protein that is produced by expression of a nucleotide sequence encoding the amino acid sequence of the protein from a recombinant DNA molecule.

The term "recombinant host cell" refers to a cell having DNA introduced from an exogenous source. Thus, for example, recombinant host cells may express genes that are not found within the native (non-recombinant) form of the cell or may express genes normally found in the cell but which have been introduced into the cell in a different manner, e.g. linked to different expression control sequences.

The terms "isolated" "purified" or "biologically pure" refer to material which is at least partially separated from and which is often substantially or essentially free from components which normally accompany it as found in its native state. Purity and homogeneity are typically determined using analytical chemistry techniques such as polyacrylamide gel electrophoresis or high performance liquid chromatography. A protein or nucleic acid molecule which is the predominant protein or nucleic acid species present in a preparation is substantially purified. Generally, an isolated protein or nucleic acid molecule will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The term "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well characterized fragments products by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies, and further includes "humanized" antibodies made by now conventional techniques.

The term "immunoassay" is an assay that utilizes an antibody to specifically bind an analyte. The immunoassay is characterized by the use of specific binding properties of a particular antibody to isolate, target, and/or quantify the analyte.

A "label" is a composition detectable by spectroscopic, photochemical, biochemical, immunochemical, or chemical means. For example, useful labels include $^{32}$P fluorescent dyes, electron-dense reagents, enzymes (e.g., as commonly used in an ELISA), biotin, dioxigenin, or haptens and proteins for which antisera or monoclonal antibodies are available can be made detectible, e.g., by incorporating a radio-label into the peptide, and used to detect antibodies specifically reactive with the peptide). A label often generates a measurable signal, such as radioactivity, fluorescent light or enzyme activity, which can be used to quantitate the amount of bound label.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

An amino acid sequence or a nucleotide sequence is "identical" to a reference sequence if the two sequences are the same when aligned for maximum correspondence over a comparison window. Optimal alignment of nucleotide and amino acid sequences for aligning comparison window may be conducted by the local homology algorithm of Smith and Waterman (1981) *Adv. Appl. Math.*, 2:482, by the homology alignment algorithm of Needleman and Wunsch (1970) *J. Mol. Biol.*, 48:443, by the search for similarity method of Pearson and Lipman (988) *Proc. Natl. Acad. Sci., U.S.A.* 85:2444, by computerized implementations of these algorithms (GAP, BESFIT, FASTA, and TFASTA in the Wisconsin Genetics Software Package Release 7.0, Genetics Computer Group, 575 Science Dr., Madison, Wis.), or by inspection. The best alignment (i.e., resulting in the highest percentage of homology over the comparison window, i.e., 150 or 200 amino acids) generated by the various methods selected. The percentage of sequence identity is calculated by comparing two optimally aligned sequences over the window of comparison, determining the number of positions at which the identical amino acid occurs in both sequences to yield the number of matched positions, dividing the number of matched positions by the total number of positions in the window of comparison (i.e., the window size), and multiplying the result by 100 to yield the percentage of sequence identity.

The term "complementary" means that one nucleic acid molecule has the sequence of the binding partner of another nucleic acid molecule. Thus, the sequence 5'-ATGC-3' is complementary to the sequence 5'-GCAT-3'.

An amino acid sequence or a nucleotide sequence is "substantially identical" or "substantially similar" to a reference sequence if the amino acid sequence or nucleotide sequence has at least 80% sequence identity, at least 85% sequence identity, at least 90% sequence identity, at least 95% sequence identity or at least 99% sequence identity with the reference sequence over a comparison window. Two sequences that are identical to each other are, of course, also substantially identical. An indication that two peptides have amino acid sequences that are substantially identical is that one peptide is immunologically reactive with antibodies raised against the second peptide. Thus, a polypeptide is substantially identical to a second polypeptide, for example, where the two peptides differ only by a conservative substitution. An indication that two nucleotide sequences are substantially identical is that the polypeptide which the first nucleotide sequence encodes is immunologically cross-reactive with the polypeptide encoded by the second nucleotide sequence. Another indication that two nucleotide sequences are substantially identical is that the two nucleic acid molecules hybridize to each other under stringent conditions. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A subject nucleotide sequence is "substantially complementary" to a reference nucleotide sequence if the complement of the subject nucleotide sequence is substantially identical to the reference nucleotide sequence.

An antibody "specifically binds to" or "is specifically immunoreactive with" a protein when the antibody functions in a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for specificity for a particular protein. A variety of immunoassay formats may be used to select antibodies specifically immunoreactive with a particular protein. For example, solid-phase ELISA immunoassays are routinely used to select monoclonal antibodies specifically immunoreactive with protein. See Harlow and Lane (1988) Antibodies, A Laboratory Manual, Cold Spring Harbor Publications, New York, for a description of immunoassay formats and conditions that can be used to determine specific immunoreactivity.

As used herein, "test compounds" may be any substance, molecule, compound, mixture of molecules or compounds, or any other composition which is suspected of being capable of inhibiting β-secretase activity in vivo or in vitro. The test compounds may be macromolecules, such as biological polymers, including proteins, polysacchrides, nucleic acids, or the like. More usually, the test compounds will be small molecules having a molecular weight below about 2 kD, more usually below 1.5 kD, frequently below 1 kD, and usually in the range from 100 to 1,000 D, and even more usually in the range from 200 D to 750 D. Such test compounds may be preselected based on a variety of criteria. For example, suitable test compounds may be selected as having known proteolytic inhibition activity. Alternatively, the test compounds may be selected randomly and tested by the screening methods of the present invention. Such test compounds will typically be administered to reaction system (as discussed hereinbelow) at a concentration in the range from about 1 nM to 1 mM, usually from about 1 μM to 1 mM. Test compounds which are able to inhibit β-secretase cleavage of APP are considered as candidates for further screening of their ability to decrease βAP production in cells and/or animals.

II. β-Secretase

β-secretase has been characterized in a number of respects, as described in detail in the Experimental section below. β-secretase has an apparent molecular weight in the range from 260 kD to 300 kD determined by gel exclusion chromatography in 0.2% hydrogenated Triton X-100. A more accurate molecular weight in the range from 60 kD to 148 kD has been determined by electrophoresis. β-secretase will bind to wheat germ agglutinin but not to concanavalin A. It has been found to have a net negative charge at pH 5 (where it does not bind to a cationic exchange material) and a net negative charge at pH 7.5 (where it binds to an anion exchange material). The β-secretase of the present invention will cleave both wild-type (normal) and the Swedish mutation of APP at the putative β-secretase cleavage site on the immediate amino-terminal side of the βAP fragment, and has been found to have a higher proteolytic activity with respect to the Swedish form of APP. Proteolytic activity appears to be at its peak at a pH from 5 to 5.5, with very low activity at pH 7.5 and above. β-secretase is resistant to many known protease inhibitors (see Table 3 in the Experimental section below). β-secretase appears to preferably recognize only those polypeptide substrates which have retained a substantial number of residues upstream and downstream from the cleavage site (from either the wild-type, Swedish, or other mutated form) of APP. As demonstrated in the Experimental section hereinafter, peptides containing as few as five residues upstream and five residues downstream from the β-secretase cleavage site will be cleaved, but require longer incubation periods and higher enzyme levels than does cleavage of peptides containing longer regions on either side of the cleavage site.

In a preferred aspect of the present invention, β-secretase cDNA has been isolated and the gene encoding the mature protein has been determined to include 1332 nucleotides, corresponding to a protein length of 444 amino acids. The amino acid sequence of the mature β-secretase protein is in [SEQ ID No.:1] and the DNA sequence is in [SEQ ID No.:2].

The β-secretase of the present invention will be provided in an isolated and purified form. By "isolated and purified," it is meant that the β-secretase has been either (1) isolated and at least partially purified from a natural source, such as human brain tissue or human 293 cells (as described in detail in the Experimental section below) or (2) is produced recombinantly or synthetically, as also described in the Experimental section. Both the amino acid sequence of the β-secretase protein and the nucleic acid sequence of the β-secretase gene have been determined, so β-secretase can be obtained from either cellular sources using known protein purification techniques or by known recombinant and chemical synthesis techniques. Contaminating proteins may be removed from the β-secretase compositions by specific techniques, including serial lectin chromatography on agarose-bound succinylated-wheat germ agglutinin (SWGA) and agarose-bound lentil lectin (LCA). These lectins, although partly binding β-secretase activity, preferentially bind other contaminating proteins in the purified fractions, and thus allow increased enrichment of the β-secretase activity. . The β-secretase will be isolated and purified to an extent sufficient to increase the β-secretase activity in the resulting composition to a useful level. In particular, the β-secretase preparations of the present invention will have sufficient activity to cleave APP and APP-containing polypeptides as described in the Experimental section below. Preferably, the β-secretase compositions of the present invention will have an activity which is at least 10-fold greater than that of a solubilized but unenriched membrane fraction from human 293 cells. More preferably, the compositions will have a β-secretase activity which is at least about 100-fold greater than that of the solubilized membrane fraction from human 293 cells. A specific method for determining β-secretase activity in units of "ng $m^{-1}$ $h^{-1}$" is described in detail in the Experimental section below (see footnote 1 to Table 1).

This invention provides purified β-secretase proteins having an amino acid sequence substantially identical to the amino acid sequence of [SEQ ID No.: 1]. In one embodiment, the "β-secretase protein" is native β-secretase, whose amino acid sequence is identical to the amino acid sequence of [SEQ ID No.:1]. Native β-secretase protein has no significant amino acid homology with any other known protein. In another embodiment, a "β-secretase" is a human allelic variant or an animal cognate of native β-secretase that can be encoded by a nucleic acid molecule that hybridizes under stringent conditions to the nucleotide sequence encoding native β-secretase of [SEQ ID No.:2] and that is isolatable from human or animal cDNA or genomic libraries. Thus a first class of β-secretase proteins will have a naturally occurring (i.e., existing in nature) amino acid sequence.

This invention also provides β-secretase protein analogs. As used herein, the term "β-secretase protein analog" refers to a non-naturally occurring polypeptide comprising a contiguous sequence fragment of at least 10 amino acids, at least 15 amino acids, at least 20 amino acids or at least 25 amino acids from the sequence of native β-secretase [SEQ ID No.:1]. In one embodiment, β-secretase protein analogs, when presented as an immunogen, elicit the production of an antibody which specifically binds to native β-secretase protein. β-secretase protein analogs optionally are in isolated form.

This invention also provides active β-secretase protein analogs that cleave β-amyloid precursor protein at the β-amyloid peptide cleavage location, i.e. at a location immediately amino-terminal to the β-amyloid peptide. These analogues will preferably have the minimum activities described above.

Active β-secretase protein analogs include β-secretase protein analogs whose amino acid sequence differs from that of native β-secretase by the inclusion of amino acid substitutions, additions or deletions (e.g., active fragments). Active fragments can be identified empirically by cutting back the protein from either the amino-terminus or the carboxy-terminus or by deleting internal sequences to generate fragments, and testing the resulting fragments for activity.

Active analogs bearing substitutions can be prepared by introducing selected amino acid substitutions into the native protein. Any substitutions where the activity is maintained or enhanced will be within the present invention, but usually the substitutions will be "conservative" as defined below. The number of substitutions is at the discretion of the practitioner, but the amino acid sequence of the resulting protein must conform to the definition of active β-secretase protein analogs, above. Conservative amino acid substitutions refer to the potential interchangeability of residues having similar side chains. For example, a group of amino acids having aliphatic side chains is glycine, alanine, valine, leucine, and isoleucine; a group of amino acids having aliphatic-hydroxyl side chains includes serine and threonine; a group of amino acids having amide-containing side chains includes phenylalanine, tyrosine, and tryptophan; a group of amino acids having basic side chains includes lysine, arginine, and histidine; and a group of amino acids having sulfur-containing side chains includes cysteine and methionine. Preferred conservative amino acids substitution groups are: valine-leucine-isoleucine, phenylalanine-tyrosine, lysine-arginine, alanine-valine, and asparagine-glutamine.

Active β-secretase protein analogs having additions include those having amino acid extensions to the amino- or carboxy-terminal end of other active fragments, as well as additions made internally to the protein.

Protein analogs that are oligopeptides can be prepared by chemical synthesis using well known methods. However, both oligopeptides and larger β-secretase proteins and protein analogs preferably are prepared recombinantly.

The β-secretase polypeptides of the present invention may also be in the form of fusion polypeptides where an active fragment of the β-secretase molecule is joined to all or a portion of another protein. Fusions may be generated with heterologous proteins (for example, a reporter polypeptide, a binding polypeptide, or the like). Fusion polypeptides may be formed either recombinantly or by synthetic methods which are well-known in the art.

The β-secretase polypeptides of the present invention may also have amino acid residues which have been chemically modified by known techniques, such as phosphorylation, sulfonation, biotinylation or the addition of other moieties. In some embodiments, the modifications will be useful for labelling reagents, purification targets, affinity ligands targeting, or the like.

III. NUCLEIC ACIDS

A cDNA molecule encoding a β-secretase protein and portions of the untranslated 5' and 3' regions has been isolated. The nucleotide sequence and deduced amino acid sequence of the nucleic acid molecule are presented in FIG. 1. [SEQ ID No.:4 and SEQ ID No.:5, respectively.] This nucleotide sequence contains an open reading frame of 1332 bases encoding native β-secretase protein from nucleotide to nucleotide. The polypeptide having the deduced amino acid sequence has a calculated molecular weight of approximately 49 kDa protein. The calculated molecular weight is without glycosylation, and is expected that the actual molecular of the glycosylated molecule is substantially higher.

Accordingly, this invention provides recombinant nucleic acid molecules comprising nucleotide sequences from the sequence encoding β-secretase protein, and nucleotide sequences that code for the expression of a β-secretase protein or β-secretase protein analog. In one embodiment, the recombinant nucleic acid molecule comprises at least 25, at least 30, at least 50, at least 100, at least 500 or at least 1000 nucleotides in a contiguous sequence in [SEQ ID No.:2].

In another embodiment, the recombinant nucleic acid molecule comprises a nucleotide sequence that codes for the expression of a polypeptide whose amino acid sequence comprises a contiguous sequence of at least 10 amino acids, at least 15 amino acids, at least 20 amino acids, at least 25 amino acids, at least 100 amino acids or at least 250 amino acids from amino acids of [SEQ ID No.:1]. In one specific embodiment, the nucleotide sequence is substantially identical to the nucleotide sequence of [SEQ ID No.:2]. In another specific embodiment, the nucleotide sequence that encodes the contiguous amino acid sequence (e.g., at least 10 amino acids) is a nucleotide sequence from [SEQ ID No.:2].

In another embodiment, the recombinant nucleic acid is an expression vehicle. In this embodiment, the recombinant nucleic acid can comprise expression control sequences operably linked to a nucleotide sequence encoding at least 10 amino acids selected from the amino acids [SEQ ID No.:1].

In yet another embodiment, the nucleotide sequence codes for the expression of a protein which when presented as an immunogen, elicits the production of an antibody which specifically binds to native β-secretase protein. Preferably, such a protein contains an amino acid sequence substantially identical to at least six contiguous amino acids of [SEQ ID No.:1], more preferably being at least nine, and even more preferably being at least twelve, and in particular includes the sequences set forth in [SEQ ID Nos:9 to 11].

The nucleic acids of the present invention may be cloned, or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a nucleic acid encoding the protein can be isolated by polymerase chain reaction of cDNA from human brain cells using primers based on the DNA sequence of β-secretase cells using primers based on the DNA sequence of β-secretase of [SEQ ID No.:2]. A wide variety of cloning and in vitro amplification methodologies are well-known to persons of skill. PCR methods are described in, for example, U.S. Pat. No. 4,683,195; Mullis et al. (1987) *Cold Spring Harbor Symp. Quant. Biol.* t1:263; and Erlich, ed., PCR Technology, (Stockton Press, NY, 1989). Nucleic acids also can be isolated by screening genomic or cDNA libraries with probes selected from the sequences of [SEQ ID No.:2] under stringent hybridization conditions, e.g., salt and temperature conditions substantially equivalent to 5×SSC and 65° C. for both hybridization and wash.

Mutant versions of the proteins may be made by site-specific mutagenesis of other nucleic acids encoding the proteins, or by random mutagenesis caused by a variety of methodologies including increasing the error rate of PCR of the original polynucleotide with 0.1 mM $MnCl_2$ and unbalanced nucleotide concentrations.

This invention also provides expression vectors, e.g., recombinant nucleic acid molecules further comprising expression and control sequences operatively linked to the nucleotide sequence coding for expression of the polypeptide. Expression vectors can be adapted for function in prokaryotes or eukaryotes by inclusion of appropriate promoters, replication sequences, markers, etc. The construction of expression vectors and expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc.

Methods of transfecting genes into mammalian cells and obtaining their expression for in vitro use or for gene therapy, are well known to the art. See e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990).

Expression vectors useful in this invention depend on their intended use. Such expression vectors must, of course, contain expression and replication signals compatible with the host cell. Expression vectors useful for expressing the protein of this invention include viral vectors such as retroviruses, adenoviruses and adeno-associated viruses, plasmid vectors, cosmids, liposomes and the like. Viral and plasmid vectors are preferred for transfecting mammalian cells. Appropriate expression control Sequences for mammalian cells include, for example, the metallothionein promoter and CMV (cytomegalovirus).

The invention also provides recombinant host cells transfected with the expression vector for expression of the nucleotide sequences coding for expression of a polypeptide of this invention. Host cells can be selected for high levels of expression in order to purify the protein. Mammalian cells insect cells, and prokaryotic cells, such as *E. coli*, can all be used for expression. The cell can be, e.g., a cultured cell or a cell in vivo.

This invention is also directed to nucleic acid probes, preferably isolated, of at least 15 nucleotides, at least 20 nucleotides or at least 25 nucleotides, that specifically hybridize with a nucleotide sequence of nucleotide sequence of [SEQ ID No.:1] or its complement, in particular, a unique sequence. As used herein "unique nucleotide sequence of [SEQ ID No.:1] refers to nucleotide sequences which were not previously known. In one embodiment, the probe has a sequence identical or complementary to a sequence of [SEQ ID No.:2]. These isolated nucleic acid molecules are useful as primers for amplification of β-secretase sequences by, e.g., PCR. They also are useful as probes in hybridization assays, such as Southern and Northern blots, for identifying nucleic acids having a nucleotide sequence of a protein of this invention. In one embodiment, the isolated nucleic acids further comprise a label.

IV. ANTIBODIES AND HYBRIDOMAS

The β-secretase polypeptides of the present invention may be used to prepare polyclonal and/or monoclonal antibodies using conventional techniques with the β-secretase polypeptides as an immunogen. The intact β-secretase molecule, or fragments thereof, optionally coupled to a carrier molecule, may be injected into small vertebrates, with monoclonal antibodies being produced by well-known methods, as described in detail below. Antibodies produced from β-secretase will be useful for performing conventional immunoassays to detect β-secretase in biological and other specimens. Antibodies according to the present invention will bind to β-secretase with an affinity of at least $10^6 \text{ M}^{-1}$, $10^7 \text{ M}^{-1}$, $10^8 \text{ M}^{-1}$, or $10^9 \text{ M}^{-1}$.

A number of immunogens can be used to produce antibodies that specifically bind β-secretase polypeptides. Recombinant or synthetic polypeptides of 10 amino acids in length, or greater, selected from sub-sequences of [SEQ ID No.:1] are the preferred polypeptide immunogen for the production of monoclonal or polyclonal antibodies. In one class of preferred embodiments, an immunogenic peptide conjugate is also included as an immunogen. Naturally occurring polypeptides can also be used either in pure or impure form.

Recombinant polypeptides are expressed in eurkaryotic or prokaryotic cells and purified using standard techniques. The polypeptide, or synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen, preferably a purified polypeptide, a polypeptide coupled to an appropriate carrier (e.g., GST, keyhole limpet hemanocyanin, etc.) or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When approximately high titers of antibody to the immunogen are obtained, blood is collected from the animal and antisera are prepared. Further fractionation of the antisera to enrich for antibodies reactive to the polypeptide is performed where desired. See e.g., Coligan (1991) *Current Protocols in Immunology* Wiley/Greene, NY; and Harlow and Lane (1989) *Antibodies: A Laboratory Manual* Cold Spring Harbor Press, NY.

Antibodies, including binding fragments and single chain recombinant versions thereof, against predetermined fragments of β-secretase proteins are raised by immunizing animals, e.g., with conjugates of the fragments with carrier proteins as described above. Typically, the immunogen of interest is a peptide of at least 3 amino acids, more typically the peptide is 5 amino acids in length, preferably, the fragment is 10 amino acids in length and more preferably the fragment is 15 amino acids in length or greater. The peptides can be coupled to a carrier protein (e.g., as a fusion protein), or are recombinantly expressed in an immunization vector. Antigenic determinants on peptides to which antibodies bind are typically 3 to 10 amino acids in length.

Monoclonal antibodies may be prepared from cells secreting the desired antibody. In some instances, it is desirable to prepare monoclonal antibodies from particular mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256:495–497. Summarized briefly, this method proceeds by injecting an animal with an immunogen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned singe B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield the monoclonal antibodies produced by such cells is enhanced by various techniques, including injection into the peritoneal cavity of a vertebrate (preferably mammalian) host. The polypeptides and antibodies of the present invention are not with or without modification, and include chimeric antibodies such as humanized murine antibodies.

Other suitable techniques involve selection of libraries of recombinant antibodies in phage or similar vectors. See, Huse et al. (1989) *Science* 246: 1275–1281; and Ward, et al. (1989) *Nature* 341: 544–546.

Frequently, the polypeptides and antibodies will be labeled by joining, either covalently or non covalently, a substance which provides for a detectable signal. A wide variety of labels and conjugation techniques are know and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,272,149; and 4,366,241. Also, recombinant immunoglobulins may be produced. See, Cabilly, U.S. Pat. No. 4,816,567; and Queen et al. (1989) *Proc. Natl'l Acad. Sci. USA* 86: 10029–10033.

The antibodies of this invention are also used for affinity chromatography in isolating β-secretase proteins. Columns are prepared, e.g., with the antibodies linked to a solid support, e.g., particles, such as agarose, Sephadex, or the like, where a cell lysate is passed through the column, washed and treated with increased concentrations of a mild denaturant, whereby purified β-secretase polypeptides are released.

The antibodies can be used to screen expression libraries for particular expression products such as mammalian β-secretase. usually the antibodies in such a procedure are labeled with a moiety allowing easy detection of presence of antigen by antibody binding.

Antibodies raised against β-secretase can also be used to raise anti-idiotypic antibodies. These are useful for detecting or diagnosing various pathological conditions related to the presence of the respective antigens.

An alternative approach is the generation of humanized immunoglobulins by linking the CDR regions of the non-human antibodies to human constant regions by recombinant 86:10029–10033 (1989) and WO 90/07861. The humanized immunoglobulins have variable region framework residues substantially from a human immunoglobulin (termed an acceptor immunoglobulin) and complementarity determining regions substantially from a mouse immunoglobulin, (referred to as the donor immunoglobulin). The constant region(s), if present, are also substantially from a human immunoglobulin. The human variable domains are usually chosen from human antibodies whose framework sequences exhibit a high degree of sequence identity with the murine variable region domains from which the CDRs are derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g., is within about 3 Å of a CDR region), or
(4) participates in the $V_L$–$V_H$ interface.

Other candidates for substitution are acceptor human framework amino acids that are unusual for a human immunoglobulin at that position. These amino acids can be substituted with amino acids from the equivalent position of the antibody or from the equivalent positions of more typical human immunoglobulins.

A further approach for isolating DNA sequences which encode a human monoclonal antibody or a binding fragment thereof is by screening a DNA library from human B cells according to the general protocol outlined by Huse et al., *Science* 246:1275–1281 (1989) and then cloning and amplifying the sequences which encode the antibody (or binding fragment) of the desired specificity. The protocol described by Huse is rendered more efficient in combination with phage display technology. See, e.g., Dower et al., WO 91/17271 and McCafferty et al., WO 92/01047. Phasge display technology can also be used to mutagenize CDR regions of antibodies previously shown to have affinity for β-secretase protein receptors or their ligands. Antibodies having improved binding affinity are selected.

In another embodiment of the invention, fragments of antibodies against β-secretase protein or protein analogs are provided. Typically, these fragments exhibit specific binding to the β-secretase protein receptor similar to that of a complete immunoglobulin. Antibody fragments include separate heavy chains, light chains Fab, Fab', F(ab')$_2$, Fabc, and Fv. Fragments are produced by recombinant DNA techniques, or by enzymic or chemical separation of intact immunoglobulins.

V. SCREENING ASSAYS

The present invention further provides assays for detecting β-secretase mediated cleavage of APP and other polypeptides substrates recognized by β-secretase. The methods utilize a reaction system which includes both a β-secretase component and a substrate component, where the β-secretase cleaves the substrate over time to produce cleavage products. Thus, β-secretase activity can be observed and monitored over time as the amount of cleavage product(s) increases. The amount of cleavage product(s) in the reaction system can be measured in a variety of ways, including immunologic, chromatographic, electrophoretic, and the like.

Such β-secretase cleavage methods are particularly useful for screening test compounds to determine their ability to inhibit β-secretase mediated cleavage of APP. In such cases, a test compound is added to the reaction system and the effect of the test compound on production of cleavage product is observed. Those compounds which inhibit the production of cleavage product(s) are considered as potential β-secretase inhibitors and further as potential therapeutic agents for treatment of conditions associated with βAP production.

The reaction system will usually comprise one of two types. First, the reaction system may comprise a β-secretase and a polypeptide substrate which are obtained separately from different sources and thereafter admixed into the reaction mixture. Usually, the β-secretase will be either a purified or partially purified β-secretase obtained from a cellular source, as described above, or will be a recombinant β-secretase, also as described above. The polypeptide substrate, in turn, will usually be either full length APP isolated from a natural source or produced recombinantly, a fragment of APP or other polypeptide which mimics a portion of APP and comprises the β-secretase cleavage site (as described in more detail below), or a synthetic peptide comprising the β-secretase cleavage site. The β-secretase and polypeptide substrate can be used in a wide variety of solid phase detection systems which permit observance of the production of β-secretase cleavage products over time.

Alternatively, the reaction system may comprise native β-secretase and native APP obtained from a single, common cellular source, usually being simultaneously extracted from cell membranes. As described in more detail in the Experimental section hereinafter, human brain or other cells may be obtained from culture, disrupted, and treated to obtain supernatants which comprise both β-secretase and native APP in amounts which permit subsequent conversion of the APP into cleavage products by the β-secretase. The cleavage products may be detected in the same way as described elsewhere in the present application, and the methods will be particularly useful for determining the ability of test compounds to inhibit such β-secretase mediated cleavage.

The first β-secretase assay described above may be performed by combining an at least partially purified β-secretase is combined with a polypeptide substrate comprising the β-secretase cleavage site of APP in the presence of the test substrate. Conditions are maintained such that the β-secretase would cleave the polypeptide substrate into an amino-terminal fragment and a carboxy-terminal fragment in the absence of a substance which inhibits such cleavage. Cleavage of the polypeptide substrate in the presence of the test compound is compared with that in the absence of the test compound, and those test substances which provide significant inhibition of the cleavage activity (usually at least about 25% inhibition, more usually at least about 50% inhibition, preferably at least about 75% inhibition, and often at least about 90% inhibition or higher) are considered to be β-secretase inhibitors. Such β-secretase inhibitors may then be subjected to further in vitro and/or in vivo testing to determine if they inhibit the production of βAP in cellular and animal models. Suitable in vivo and in vitro tests are described in U.S. Pat. No. 5,538,845 the full disclosures of which are incorporated herein by reference.

Suitable substrate polypeptides will include a region of the APP molecule which is recognized and cleaved by β-secretase. Usually, the substrate polypeptide will include at least about 5 amino acid residues, and preferably at the least about 17 amino acids, amino-terminal to the cleavage site (located between amino acids 596 and 597 in the 695-amino acid APP isomer) and at least about 5 amino acids, preferably at least about 16 amino acids, and most preferably at least 42 amino acids (i.e., the full βAP sequence), on the carboxy-terminal side of the cleavage site. The cleavage site will typically comprise the Met-Asp or the Leu-Asp cleavage site characteristic of the wild-type and Swedish forms of βAPP. An intact APP molecule will be suitable as the polypeptide including both wild-type and mutant forms of APP, particularly including the Swedish mutation of APP. Use of fusion substrate polypeptides is often preferred, where an affinity region can be fused to the β-secretase cleavage site of APP, producing a molecule whose cleavage can be conveniently monitored in solid phase test systems.

The screening assays of β-secretase and suitable substrate polypeptide are conveniently performed using "sandwich" assays where the amino-terminal or the carboxy-terminal fragment produced by cleavage is captured on a solid phase. The captured fragment may then be detected using an antibody specific for the end of the fragment exposed by β-secretase cleavage. In an exemplary embodiment described in detail in the Experimental section below, the polypeptide substrate is a fusion polypeptide combining maltose-binding protein and a 125-amino acid carboxy-terminal fragment of APP. The assay uses anti-maltose-binding protein antibody to capture the amino-terminal cleavage product, where the carboxy-terminus of the cleavage product is detected by an antibody specific thereto. An exemplary antibody is 192 antibody or SW-192 antibody, described in more detail in U.S. Pat. No. 5,604,102, the full disclosure of which is incorporated herein by reference. The binding of the antibody to the cleaved fusion polypeptide is detected using conventional labelling systems, such as horseradish peroxidase or other detectable enzyme labels, which are bound to the antibody directly (covalently), or indirectly through intermediate linking substances, such as biotin and avidin.

VI. Pharmaceutical Compositions and Therapeutic Methods

The present invention further comprises methods for inhibiting the β-secretase mediated cleavage of APP to APP cleavage products in cells, where the method comprises administering to the cells compounds selected by the method described above. The compounds may be added to cell culture in order to inhibit APP cleavage which results in βAP production of other cultured cells. The compounds may also be administered to a patient in order to inhibit β-secretase mediated APP cleavage which results in pathogenic βAP production and the deposition of amyloid β-plaque associated with Alzheimer's Disease and other βAP-related conditions.

The present invention further comprises pharmaceutical compositions incorporating a compound selected by the above-described method and including a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, Remington's Pharmaceutical Sciences, Mack Publishing Company, Easton, Pa., 16th Ed., 1982, the disclosure of which is incorporated herein by reference.

The pharmaceutical compositions just described are suitable for systemic administration to the host, including both parenteral and oral administration. The pharmaceutical compositions will usually be administered parenterally, i.e. subcutaneously, intramuscularly, or intravenously. Thus, the present invention provides compositions for administration to a host, where the compositions comprise pharmaceutically acceptable solution of the identified compound in an acceptable carrier, as described above.

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid-soluble and amenable to transportion across the blood-brain barrier. Alternatively, the delivery of hydrophilic drugs can be enhanced by intra-arterial infusion of hypertonic solutions which can transiently open the blood-brain barrier.

The concentration of the compound in the pharmaceutical carrier may vary widely, i.e. from less than about 0.1% by weight of the pharmaceutical composition to about 20% by weight, or greater. Typical pharmaceutical composition for intramuscular injection would be made up to contain, for example, one to four ml of sterile buffered water and one $\mu$g to one mg of the compound identified by the method of the present invention. The typical composition for intravenous infusion could be made up to contain 100 to 500 ml of sterile Ringer's solution and about 1 to 100 mg of the compound.

The pharmaceutical compositions of the present invention can be administered for prophylactic and/or therapeutic treatment of diseases related to the deposition of $\beta$AP, such as Alzheimer's disease, Down's syndrome, and advanced aging of the brain. In therapeutic applications, the pharmaceutical compositions are administered to a host already suffering from the disease. The pharmaceutical compositions will be administered in an amount sufficient to inhibit further deposition of $\beta$AP plaque. An amount adequate to accomplish this defined as a "therapeutically effective dose." Such effective dose will depend on the extent of the disease, the size of the host, and the like, but will generally range from about $\mu$g to 10 mg of the compound per kilogram of body weight of the host, with dosages of 0.1 $\mu$g to 1 mg/kg being more commonly employed.

For prophylactic applications, the pharmaceutical compositions of the present invention are administered to a host susceptible to the $\beta$AP-related disease, but not already suffering from such disease. Such hosts may be identified by genetic screening and clinical analysis, as described in the medical literature (e.g. Goate (1991) Nature 349:704–706). The pharmaceutical compositions will be able to inhibit or prevent deposition of the $\beta$AP plaque at a symptomatically early stage, preferably preventing even the initial stages of the $\beta$-amyloid disease. The amount of the compound required for such prophylactic treatment, referred to as a prophylactically-effective dosage, is generally the same as described above for therapeutic treatment.

The following examples are offered by way of illustration, not by way of limitation.

EXPERIMENTAL

Purification and Characterization of $\beta$-Secretase

Frozen tissue (293 cell paste or human brain) was cut into pieces and combined with five volumes of homogenization buffer (20 mM Hepes, pH 7.5, 0.25 M sucrose, 2 mM EDTA). The suspension was homogenized using a blender and centrifuged at 1000×g (10 min, 4° C.) to produce a post-nuclear supernatant which was saved on ice. The pellets were resuspended in fresh homogenizing buffer at the original volume, and the centrifugation step was repeated. The second supernatant was combined with the first one, and the supernatant pool ("PNS") was centrifuged at 16,000×g for 30 min at 4° C. The supernatants were discarded and the pellets, labelled "P2," were either used immediately for enzyme purification or frozen at −40° C. for later use.

The pellets were suspended in extraction buffer (20 mM MES, pH 6.0, 0.5% Triton X-100, 150 mM NaCl, 2 mM EDTA, 5 $\mu$g/ml leupeptin, 5 $\mu$g/ml E64, 1 $\mu$g/ml pepstatin, 0.2 mM PMSF) at the original volume. After vortex-mixing, the extraction was completed by agitating the tubes at 4° C. for a period of one hour. The mixtures were centrifuged as above at 16,000×g, and the supernatants were pooled. The pH of the extract was adjusted to 7.5 by adding ~1% (v/v) of 1 M Tris base (not neutralized).

The neutralized extract was loaded onto a wheat germ agglutinin-agarose (WGA-agarose) column pre-equilibrated with 10 column volumes of 20 mM Tris, pH 7.5, 0.5% Triton X-100, 150 mM NaCl, 2 mM EDTA, at 4° C. One milliliter of the agarose resin was used for every 4 g of original tissue used. The WGA-column was washed with 10 column volumes of the equilibration buffer, and then eluted as follows. Three-quarter column volumes of 1 M N-acetylglucosamine in 20 mM Tris, pH 7.5, 0.5% Triton X-100, 2 mM EDTA were passed through the column after which the flow was stopped for fifteen minutes. An additional five column volumes of the 1 M N-acetylglucosamine elution buffer were then used to elute the column, followed by five column volumes of 1% chitin hydrolysate in 20 mM Tris, pH 7.5, 0.5% Triton X-100, 2 mM EDTA. All of the above eluates were combined (pooled WGA-eluate).

The pooled WGA-eluate was diluted 1:4 with 20 mM NaOAc, pH 5.0, 0.5% Triton X-100, 2 mM EDTA. The pH of the diluted solution was adjusted to 5.0 by adding a few drops of glacial acetic acid while monitoring the pH. This "SP load" was passed through a 5-ml Pharmacia HiTrap SP-column equilibrated with 20 mM NaOAc, pH 5.0, 0.5% Triton X-100, 2 mM EDTA, at 4 ml/min at 4° C. $\beta$-Secretase activity was present in the flow-through fraction, which was neutralized by adding enough 1 M Tris (not neutralized) to bring the pH up to 7.5. The enzyme solution was then loaded onto a 1-ml Pharmacia HiTrap Q-column equilibrated with approximately 10 column volumes of 20 mM Tris, pH 7.5, 0.2% hydrogenated Triton X-100, 2 mM EDTA, at 1.5 ml/min at 4° C. The column was washed with 10 column volumes of 20 mM Tris, pH 7.5, 0.2% hydrogenated Triton X-100, 50 mM NaCl, 2 mM EDTA. Protein was eluted using a linear gradient from 50 mM TO 350 Mm NaCl over 30 minutes at a flow-rate of 1 ml/min at 4° C. The protein concentrations in the HiQ fractions were measured using a BioRad colorimetric protein assay, and the $\beta$-secretase activity was measured using the MBP-C125 cleavage assay at pH 5.5. The fractions in the ascending portion of the protein peak have the highest specific activity and were pooled for further purification of the enzyme.

The pooled fractions from the HiTrap Q were then applied to a column of concanavalin A-agarose (10% v/v of pool) equilibrated with 10 column volumes of 20 mM Tris, pH 7.5, 0.2% hydrogenated Triton X-100, 150 mM NaCl, 2 mM EDTA. The Con A flow-through was then loaded onto a Superdex 200 (26/60) gel exclusion chromatography column, which was eluted with Tris buffered saline, pH 7.4, 0.2% hydrogenated Triton X-100, 2 mM EDTA, at 1 ml/min, collecting 3 min/fraction. Fractions containing $\beta$-secretase activity were identified using the MBP-C125 cleavage assay.

The apparent molecular weight of the β-secretase activity eluting from the Superdex column was estimated from the peak elution volume (relative to that of standard proteins) to be 280,000±9800 (average of two runs for 293 cells, and two runs for human brain).

Results from a large-scale preparation of the enzyme from human brain tissue is shown in Table 1 below.

TABLE 1

| Step | Acitivity ng/ml/h | Protein μg/ml | Sp. Act.[1] ng/ml/h/μg protein | Fold Purfn. |
|---|---|---|---|---|
| Solubilized membrane extr. | 2700 | 350 | 7.7 | 1 |
| HiQ Elution pool | 80000 | 210 | 380.9 | 49.5 |
| Con A Flow-Thru | 80000 | 100 | 800 | 103.8 |
| Superdex peak fraction | 57000 | <5 | >11400 | >1480.5 |

[1]Specific activity of the purified β-secretase was measured as follows. MBP C125-SW (described below) was combined at approximately 0.7 μg/ml in 100 mM sodium acetate, pH 5.5, with 0.3% Triton X-100. The amount of product generated was measured by the β-secretase assay, also described below. Specific activity was then calculated as:

$$\text{Sp. Act.} = \frac{(\text{Product conc. ng/ml})(\text{Dilution factor})(\text{Incubation vol. } \mu l)}{(\text{Enzyme sol. vol. } \mu l)(\text{Incubation time h.})(\text{Enzyme conc. } \mu g/ml)}$$

The Sp. Act. is thus expressed as ng of protein produced per μg of β-secretase per hour.

Glycosylation of β-secretase has been investigated using various immobilized lectins, and ability of substantially purified β-secretase activity to bind to them was determined. Table 2 summarizes this data. A "−" sign signifies less than 20% binding, "+" between 24–40% binding, "++" between 50–75% binding, and "+++" >75% binding.

TABLE 2

| Lectin | β-Secretase Binding |
|---|---|
| jeguirity bean (APA) | + |
| jack bean (con A) | + |
| scotch broom (CSA) | + |
| jimson weed (DSA) | + |
| coral tree (ECA) | − |
| grifornia simplicifolia I | − |
| grifornia simplicifolia II | − |
| Jacalin (AIA) | + |
| lentil (LCA) | + |
| horseshoe crab (LPA) | − |
| tomato (LEL) | + |
| maackia (MAA) | + |
| peanut (PNA) | + |
| pokeweed (POA) | − |
| castor bean (RCA1) | − |
| potato (STL) | − |
| wheat germ-succinylated (SWGA) | + |
| China gourd (TKA) | + |
| stinging nettle (UDA) | + |
| gorse (UEAI) | − |
| gorse (UEAII) | − |
| hairy vetch (VVL) | − |
| wheat germ (WGA) | +++ |

Only a single lectin (WGA) bound β-secretase activity quantitatively, out of the many tested. Partial binding of the activity (25–40%) to a number of other lectins probably indicates heterogeneous glycosylation.

β-secretase purified as described was assayed in the presence of a number of common protease inhibitors as follows. Enzyme solution was mixed with the inhibitor, as described below in the β-Secretase Inhibitor Assay section, and assayed for activity remaining as a percentage of a control solution incubated under otherwise identical conditions. $IC_{50}$ values, if any, were determined as the concentration of inhibitor which resulted in 50% inhibition of the control activity. The results are set forth in Table 3.

TABLE 3

| Inhibitor | Max Conc | IC50 |
|---|---|---|
| SERINE PROTEASES | | |
| aminoethylbenzene-sulfonyl fluoride | 0.8 mM | NI |
| chyrnostatin | 0.2 mM | NI |
| 3,4-dichloroisocoumarin | 0.5 mM | <25% inh. |
| diisopropylfluoro-phosphate | 2 mM | NI |
| elastatinal | 0.2 mM | NI |
| phenylmethylsulfonyl-fluoride | 1.0 mM | NI |
| CYSTEINE PROTEASES | | |
| E-64 | 0.14 mM | NI |
| N-ethylmaleimide | 10 mM | NI |
| iodoacetamide | 10 mM | NI |
| METALLOPROTEASES | | |
| EDTA | 2 Mm | NI |
| phosphoramidon | 10 mM | NI |
| o-phenanthroline | | 7 mM |
| m-phenanthroline | | 7 mM |
| ASPARTYL PROTEASES | | |
| pepstatin | 25 μM | NI |
| diazoacetylnorleucyl-methyl ester | | >5 mM |
| DIVALENT METAL IONS | | |
| Cu | | 2 mM |
| Zn | | 3 mM |
| Hg | | −10% inh |
| Ca | | NI |
| Mg | | NI |

These results indicate that β-secretase activity is not inhibited by common inhibitors of serine, cysteine, aspartyl, and metalloproteases. Although o-phenanthroline inhibits poorly, m-phenanthroline, which is not a metal chelator, also does so, suggesting that this weak inhibition is unrelated to the metal-chelating properties of o-phenanthroline.

Partial Sequencing, Production of Synthetic Peptides, and Production of Antibodies The Superdex elution fractions containing the peak of β-secretase activity described above in connection with Table 1 were pooled and passed through a 1-ml succinylated wheat germ agglutinin agarose (SWGA-agarose, Vector Labs) column. The SWGA column had been previously washed with 5 column volumes of Tris-buffered saline, pH 7.4, 0.2% hydrogenated Triton X-100, 1 mM CaCl2, 1 mM MgCl2, followed by 5 column volumes of the same buffer with 1 M NaCl, and finally 10 column volumes of the first, low [NaCl] buffer. After the enzyme sample had been passed through the SWGA column, the resin was washed with an additional one-half column volume of the equilibration buffer. The flow through from this was pooled with the sample flow-through containing the bulk of the β-secretase activity.

The SWGA-agarose flow-through was then passed through a 1 ml lentil lectin agarose column (LCA-agarose, lens culinaris agglutinin, Vector Labs) washed and equilibrated as described above for the SWGA resin. The majority of the β-secretase activity is again recovered in the LCA flow-through fraction.

The LCA flow-through was then diluted 1:4 with 20 mM Tris, pH 7.5, 2 mM EDTA, 0.2% hydrogenated Triton X-100, and allowed to bind to 40 μl of DEAE-Sepharose Fast Flow (Pharmacia), by mixing the enzyme solution with the anion-exchange resin at 4° C. overnight, with gentle agitation. The DEAE-Sepharose resin is then recovered by centrifugation, washed once with the dilution buffer, and the bound enzyme eluted with 200 μl of the dilution buffer containing 450 mM NaCl. The eluted enzyme solution was divided into two unequal parts, 20% and 80%, and each part was electrophoresed under non-denaturing conditions into a 6% separating—4% stacking native gel system, in adjacent lanes, according to the method of Laemmli (Nature, 227, 680 (1970), except that the SDS is replaced by 0.2% hydrogenated Triton X-100. Following electrophoresis, the gel was soaked for ~30 minutes in 0.1 M sodium acetate, pH 5.5. The "analytical" (20%) and "preparative" lanes of electrophoresed enzyme (each 7 cm long×1 cm wide×1 mm thick) were then cut into ~2.5 mm pieces using a clean razor blade, sequentially from the top of the stacker to the bottom of the separating gel. Each of the analytical slices was combined with 60 μl water and 10 μl 1 M sodium acetate in a microcentrifuge tube, then homogenized using a Kontes Deltaware motorized pellet pestle microhomogenizer. MBP-C125SW was added to the desired concentration (0.5–0.7 ug/ml), and the mixture incubated overnight. The samples are then diluted with specimen diluent 50-fold, and analyzed by the beta-secretase activity ELISA described below. Preparative slices corresponding to those analytical slices containing β-secretase activity were then processed as described below to generate tryptic fragments from the gel-purified enzyme to obtain partial protein sequence.

Gel slices containing β-secretase activity were first reduced and alkylated, then digested with trypsin. Peptides were extracted from the gel pieces and separated by reverse phase HPLC. Collected purified peptides were sequenced by automated Edman degradation. Experimental methods follow. Each preparative gel slice was diced into pieces approximately 1 mm square. To facilitate handling, the diced pieces of each slice were loaded into individual microfuge tubes. Pieces were washed twice with 100 μl cold absolute ethanol per tube. The shrunken pieces were then rehydrated in a volume of Reducing Buffer (0.1M ammonium bicarbonate, 0.2% hydrogenated Triton X-100, and 0.1M DTT) sufficient to have about 2 mm of liquid above the pieces, typically 130–150 μl. The tubes were then incubated at 50° C. for 30 min with shaking. Following reduction, the pieces were alkylated by the addition of 25% v/v of 0.5M iodoacetic acid, usually about 35 μl. The tubes were then incubated on ice, in the dark with shaking, for 45 min. Excess reagents were removed and the pieces partially reshrunken by addition of sufficient cold absolute ethanol to adjust liquid to 80% ethanol. The tubes containing the gel pieces and ethanol solution were then chilled briefly at −20° C., while the trypsin was prepared.

To one vial containing 20 μg of modified, sequencing grade trypsin (Promega) was added 50 μl reconstitution buffer (Promega). After trypsin had completely dissolved, an aliquot of 12.5 μl was removed and added to 37.5 μl of Digestion Buffer (0.1M ammonium bicarbonate, 0.2% hydrogenated Triton X-100), yielding a trypsin concentration of 1 μg/10 μl. The tubes containing the gel pieces were centrifuged briefly, and the ethanol solutions removed. A further 100 μl of absolute ethanol was added to each tube to shrink and dehydrate gel pieces. The tubes were spun and the ethanol removed. To each Mg NI tube was added about 20 μl of Digestion Buffer in order to just wet the shrunken gel pieces. Immediately, 10 μl of prepared trypsin solution was added to each tube. (This allows the pieces to absorb the trypsin solution completely.) Sufficient Digestion Buffer was added to leave about 2 mm on top of gel pieces. The tubes were then incubated at 37° C. with gentle shaking for about 2 hr. The buffer level was checked and more Digestion Buffer was added as necessary to maintain the 2 mm excess. Incubation was allowed to proceed overnight (~14 hr). Tubes were checked and spun briefly to return condensate to the bottoms, and more Digestion Buffer was added if necessary. After about 20 hr, a second aliquot of freshly prepared trypsin solution (as described above) was added, and the digestion allowed to proceed for a total of about 36 hr at 37° C.

Tubes were taken from 37° C. shaker and centrifuged. The supernatants were removed, combined into a 2 ml microfuge tube and acidified with trifluoroacetic acid(TFA,double-distilled). The gel pieces, still in individual tubes, were then extracted sequentially with 100 μl Digestion Buffer; 100 μl 30% acetonitrile(AcN), 0.1% TFA; and 2×100 μl 60% AcN, 0.1% TFA. Each extraction proceeded for 10 min at 37° C. with shaking. Extracts were added to combined pool described above. Between extract additions, the pooled volume was reduced in a Speed-Vac. After the second 60% AcN, 0.1% TFA extract, the shrunken gel pieces were rehydrated for 1–2 min in about 20 μl Digestion Buffer, then immediately extracted for a third time with 60% AcN, 0.1% TFA. This final extract was combined with the others, and the volume of the pooled extracts was reduced to about 350 μl. TFA (as above) was added to a final concentration of 1%.

Extracted peptides were loaded onto a Vydac C18 column, 2.1×150 mm, equilibrated at 40° C. in 0.1% TFA, 2% AcN. Purified peptides were eluted with an AcN gradient. Fractions were collected either by hand or automatically.

Selected peptide fractions were sequenced using an Applied Biosystems Model 477, equipped with a micro cartridge. Three unambiguous peptide sequences were obtained, indicated as shown:
1 AYLTV LGVPE KPQIS GFS(R) [SEQ ID No.:6]
2 IIPST PFPQE GQPLI LTCE(R) [SEQ ID No.:7]
3 GKPLP EPVL WTK [SEQ ID No.:8]

Synthetic peptides corresponding to part or all of the above three peptide sequences obtained were generated using solid-phase peptide synthesis, with the addition of an amino-terminal linker sequence for two of them (shown underlined), as indicated below:

| Peptide Name | Sepuence |
|---|---|
| Seek-1 | $NH_2$CGGYL TVLGV PEKPQ I $CONH_2$ [SEQ ID No.:9] |
| Seek-2 | AcNHIIP STPFP QEGQP LILTC $CO_2$H [SEQ ID No.: 10] |
| Seek-3 | $NH_2$CGGKP LPEPV LWTK $CONH_2$ [SEQ ID No.: 11] |

The synthetic peptides were then conjugated to cationized bovine serum albumin, prior to injection into rabbits for the generation of specific antisera. Antisera obtained at 4 and 10 weeks were then used at 1:500 in a Western blot against partially purified β-secretase. Partially purified β-secretase (Superdex fraction) was electrophoresed into 10–20% Tricine gels under either reducing or non-reducing conditions. Following transfer of the proteins to PVDF membranes, individual lanes are excised, and separately probed with pre-immune serum, and serum obtained at 4 and 10 weeks, from rabbits immunized with the three separate peptide immunogens. The Western blots are developed with secondary donkey-anti rabbit IgG, horseradish peroxidase-linked whole antibody (Amersham), diluted at 1:5000, followed by ECL (Amersham). The results from representative exposures are shown in FIG. 2 (non-reduced) and FIG. 3 (reduced). Individual lanes are marked in both figures. Specific antisera to all three synthetic peptides recognize the same protein band(s) migrating with intermediate mobility between the 60 and 148 kDa molecular weight markers. No immunoreactive bands are detected with pre-immune serum in all cases. The strongest reactivities on western blot were detected with the specific antisera to Seek-1 (Rabbit 205-A Wk 10) and Seek-3 (Rabbit 211-A Wk 10), with antisera to Seek-2 (Rabbit 210-A Wk 10) producing a much weaker signal. In all cases, much stronger immunoreactivities were evident when the protein was electrophoresed under reducing conditions as compared to non-reducing conditions. This suggests that reducing conditions favor increased exposure of the antigenic epitopes on the otherwise denatured protein, and this was taken into consideration in the design of the immunoprecipitation experiments described below.

A HiTrap Q chromatography fraction containing β-secretase activity was divided in two parts. One of the two aliquots was treated with the reducing agent dithiothreitol (DTT) at 5 mM for 30 min at room temperature. Both the reduced and the untreated, control sample were diluted 10-fold in 20 mM Tris pH 7.5, 2 mM EDTA, 0.2% hydrogenated Triton X-100. Pharmacia Protein A-Sepharose CL-4B was reconstituted by suspending the desiccated resin in the dilution buffer at 75 mg/ml, and letting it stand for 30 min on ice. Enzyme aliquots (100 μl) were then mixed with 20 μl of the reconstituted Protein A-Sepharose and 5 μl of either preimmune rabbit antisera, or antisera from rabbit 205-A Wk 10, or rabbit 211-A Wk 4, and the mixtures incubated for 2 h at room temperature, with gentle end-over-end inversion. Following sedimentation of the Protein A-Sepharose beads (plus bound antibodies and antigens) by microcentrifugation of the incubation mixtures, β-secretase activity was measured in the cleared supernatants using the MBP C125Sw assay. The results are graphically indicated in FIG. 4. The specific antisera against both peptides Seek-1 and Seek-2 immunoprecipitate β-secretase activity under reducing conditions, but not under non-reducing conditions. These results were in agreement with the previous observation that optimal epitope exposure for both antisera require prior reduction of the protein. The immunoprecipitation of β-secretase activity under the conditions of optimal epitope exposure with specific antisera raised to synthetic peptides derived from the non-denaturing gel-purified enzyme confirms that these unique peptide sequences arise from the β-secretase polypeptide.

In order to generate an amino-terminal protein sequence, it was necessary to alter the native β-secretase by chemical and enzymatic modification to permit separation of minor impurities in the preparation. In order to achieve this, mild reduction, followed by alkylation and partial deglycosylation, was carried out as described below. No loss of enzymatic activity was seen with this sequence of treatments. The LCA-agarose flow-through fraction was concentrated ~5-fold by lyophilization in a SpeedVac vacuum centrifugation apparatus. The reducing agent dithiothreitol (DTT) was added to the enzyme solution to a final concentration of 5 mM, and the preparation incubated at room temperature for 1 h. The carboxamidomethylation reagent iodoacetamide was then added to a final concentration of 10 mM, followed by a further 30 min incubation at room temperature. The treated enzyme sample was then immediately desalted using a Pharmacia PD-10 column in order to exchange the buffer to 20 mM Tris, pH 7.5, 2 mM EDTA, 0.2% hydrogenated Triton X-100 for the next treatment step.

In order to achieve the removal of Asn-linked sugar chains, 25 mU of the deglycosylating enzyme PNGase F (Glyko) was added to the β-secretase preparation. This treatment step was carried out overnight (16 h) at room temperature.

After β-secretase had thus been reduced, carboxamidomethylated, and (at least partially) deglycosylated, the treated enzyme was again subjected to anion-exchange chromatography on a 1 ml HiTrap Q column as described previously. Eluted fractions containing the peak of activity were individually concentrated by acetone precipitation, by combining 0.36 ml of each fraction with 1.44 ml of ice-cold acetone, storing the mixture overnight at −40 C, and centrifuging the samples at maximum speed on a benchtop Eppendorf microcentrifuge for 10 min. After removal of the supernatant liquid, the pellets were dried down in the SpeedVac vacuum centrifuge apparatus, and the precipitated protein pellets dissolved in Laemmli sample buffer containing 2% β-mercaptoethanol. The samples were analyzed by electrophoresis on a Novex 10–20% acrylamide Tricine gel system, following which the protein bands were visualized using Novex Colloidal Coomassie stain, using the protocol supplied by the manufacturer. An image of the stained gel was recorded using a Molecular Dynamics Personal Densitometer. In order to identify the protein bands corresponding to β-secretase, a Western blot analysis of a similar gel run in parallel, but with less protein per lane, was carried out after transfer to PVDF membranes. The Western blot was probed with antisera against peptide Seek-3 from the previously described rabbit 211-A wk 10. The results showed that the triplet of protein bands migrating immediately above the 60 kDa MW marker was strongly immunoreactive with this previously characterized antisera.

Fractions containing β-secretase activity (#'s 21–25) were acetone precipitated. Pellets were dried briefly in a SpeedVac to remove residual acetone, dissolved in SDS-PAGE loading buffer and subjected to SDS-PAGE on a 10–20% Tris-Tricine gel (Novex). The gel was transferred onto Pro-Blott membrane (Applied Biosystems) in CAPS buffer. After Coomassie blue staining, three closely spaced bands in the approximate molecular weight range of 65–75 kDa, which coincided in electrophoretic mobility with the immunoreactivity described above, were excised for protein sequencing on an Applied Biosystems Model 477. Two of the bands yielded the same major amino-acid sequence. While the first cycle could not be identified positively, the next fifteen cycles were called with reasonable certainty. The consensus sequence obtained was

[S/F/G]KNKVK GSQGQ FPLTQ XVTVV [SEQ ID No.:12]

Isolation and Sequencing of β-Secretase cDNA

A human frontal cortex brain cDNA library (Stratagene catalogue #936212) was screened with the antibody to Seek-1 (205-A Wk 10) using the Stratagene PicoBlue™ Immunoscreening Kit (Catalog#200371) according to the manufacturers's instructions with the following changes:

1) 4.0×10⁴ pfu (plaque forming units) of phage were plated per 150 mm petri dish.
2) The plated phage were incubated at 37° C. for about 6 hrs until plaques were established.
3) The plates were kept at 37° C. while the IPTG-treated nitrocellulose membrane filters were placed onto the plates.
4) After applying the first IPTG-treated nitrocellulose filter, the plates were incubated for 7 hrs at 37° C.
5) After removal of the first filter, the plates were overlayed with another set of IPTG-treated nitrocellulose filters and incubated overnight at 37° C.
6) After being removed from the plates, the filters were washed briefly in TBST and then incubated in 5 mM DTT, +1% SDS, for 20 minutes in order to reduce and denature the proteins. (In subsequent studies, this treatment step was found to be unnecessary).
7) The filters were blocked overnight at 4° C.
8) The filters were exposed to antibody to Seek-1 (205-AWk 10) at 2 µg/ml for 3 hrs.
9) The filters were incubated with substrate in color-development solution for more than 1 hour in order to see a signal.

Five plaques positive for the Seek-1 antibody were obtained, purified, and plasmids were generated using the Strategene single-clone excision protocol for clones in ZAP derived vectors. Plasmid DNA of the clone was obtained, and the DNA sequenced by standard techniques. One of these clones, designated A2, contained sequence which encoded all three sequenced peptides of the purified β-secretase protein.

The A2 clone was digested with Xho1 and Pst1, subjected to agarose gel electrophoresis, and a 329 bp DNA fragment was isolated using QIAquick Gel Extraction Kit from QIAGEN Inc. catalogue #28704. This DNA fragment was labeled with [32P]dCTP using DECAprime II™, DNA Labeling Kit from Ambion Inc. catalogue #1454, and used to probe the human frontal cortex brain cDNA library (Strategene catalogue #936212). 1×10⁶ pfu (plaque forming units) of phage were screened with the high specific activity probe (2×10⁹ CPM/µg) using standard methods (as in "Molecular Cloning, A Laboratory Manual" by T. Maniatis). The hybridization temperature was 65° C. and high stringency wash conditions (0.1×SSC, 0.1%SDS, 65° C.) were used.

One plaque positive for hybridization with the DNA probe was purified and DNA generated as described above. Sequencing of the DNA showed overlap with the A2 clone and additional 5' sequence. The two sequences were merged and are shown in FIG. 1 [SEQ. ID Nos.:4 and 5]. The initial clone, A2, starts at position 91 of that figure.

This sequence encodes a protein that contains all of the residues obtained by sequencing of the purified β-secretase protein. An analysis of the predicted hydrophobicity of the encoded protein indicated the presence of a region that could likely be a transmembrane region, and also a region that appears to encode a signal peptide sequence. These regions, and the mature protein region determined by N-terminal sequencing are all shown on FIG. 1.

β-Secretase Inhibitor Assays

1. Assays Utilizing Purified β-Secretase and Recombinant Fusion Peptide Substrates β-secretase assays utilizing the SW-192 antibody, which recognizes the free . . . Val-Asn-Leu-COOH terminal sequence uncovered by proteolytic cleavage immediately amino-terminal of the βAP sequence, were performed. Two recombinantly-expressed variants of APP (FIGS. 5 and 6) have been used as substrates for β-secretase. Both variants may be prepared as wild type or Swedish mutations. The preferred substrate (FIG. 5) was expressed in *E. coli* as a fusion protein of the carboxy terminal 125 aa of APP (APP C-125) fused to the carboxy-terminal end of maltose-binding protein (MBP), using commercially available PMAL vectors from New England Biolabs. The β-cleavage site was thus 26 amino acids downstream of the start of the APP C-125 region.

Recombinant proteins were generated with both the wild-type APP sequence (MBP-C125 WT) at the cleavage site ( . . . Val-Lys-Met-Asp-Ala . . . ) [SEQ ID No.:13] or the "Swedish" double mutation (MBP-C125 SW) ( . . . Val-Asn-Leu-Asp-Ala . . . ) [SEQ ID No.:14]. The entire sequence of the recombinant protein with the Swedish sequence is given in FIG. 7 [SEQ ID No.:3]. As shown in FIG. 5, cleavage of the intact MBP-fusion protein results in the generation of a truncated amino-terminal fragment, with the new SW-192 Ab-positive epitope uncovered at the carboxy terminus. This amino-terminal fragment can be recognized on Western blots with the same Ab, or, quantitatively, using an anti-MBP capture-biotinylated SW-192 reporter sandwich format, as shown in FIG. 5.

Anti-MBP polyclonal antibodies were raised in rabbits (Josman Labs, Berkeley) by immunization with purified recombinantly expressed MBP (New England Biolabs). Antisera were affinity purified on a column of immobilized MBP.

Fusion peptides comprising the carboxy terminal 125 amino acids of both the Swedish mutation and wild type of APP (designated MBP-C125 SW and MBP-C125 WT, respectively) were prepared from transfected *E. coli* induced with IPTG, harvested, and lysed as described in the New England Biolabs protocol, except that cells were sonicated in lysis buffer containing 150 mM sodium chloride, 50 mM Tris, pH 7.5, 5 mM EDTA, and 0.1% Triton X-100. The sonicated cells were pelleted at 10,000×g for 10 minutes at 4° C. and extracted overnight with 7 M urea, 10 mM Tris, pH 7.5, 5 mM EDTA, and 0.1% Triton X-100. The extract was cleared by centrifugation at 10,000×g for 10 minutes, then dialyzed overnight against lysis buffer. The dialyzed extract was recentrifuged as above and applied to a column of amylose resin (New England Biolabs). The column was washed extensively (at least 10 column volumes) with lysis buffer, then with two column volumes of low salt buffer (10 mM Tris, pH 7.5, 5 mM EDTA, 0.1% Triton X-100), and the product was eluted with 10 mM maltose in low salt buffer. The purified substrates were stored frozen at −40° C. in 3 M guanidine-HCl and 0.5–0.7% Triton X-100, at 0.5–1.0 mg/ml.

Microtiter 96-well plates were coated with purified anti-MBP antibody (@ 5–10 µg/ml), followed by blocking with human serum albumin. β-secretase solution (1–10 µl) was mixed with MBP-C125 SW substrate (0.5 µl) in a final volume of 50 µl, with a final buffer composition of 20 mM sodium acetate, pH 5.5, 0.035%–0.05% Triton X-100, in uncoated individual wells of 96-well microtiter plates, and incubated at 37° C. for 2 h. For inhibition screening assays, the amount of β-secretase added was adjusted to give 1600–3200 ng/ml/hr of product. Samples were then diluted 5-fold with Specimen Diluent (0.2 g/l sodium phosphate monobasic, 2.15 g/l sodium phosphate dibasic, 0.5 g/l sodium azide, 8.5 g/l sodium chloride, 0.05% Triton X-405, 6 g/l BSA), further diluted 10–20 fold into Specimen Diluent on anti-MBP coated plates, and incubated for 2 h. Biotinylated SW192 antibodies were used as the reporter. SW192 polyclonal antibodies were biotinylated using NHS-biotin (Pierce), following the manufacturer's instruction. The biotinylated antibodies were used at about 60–800 ng/ml, the exact concentration was optimized against MBP-26SW standards (see below) for each lot of antibodies used. Following incubation of the plates with the reporter, the ELISA was developed using streptavidin-labeled alkaline phosphatase (Boeringer-Mannheim) and 4-methylumbelliferyl phosphate as fluorescent substrate. Plates were read in a Cytofluor 2350 Fluorescent Measurement System. Peptides containing maltose-binding protein (MBP) fused to the wild-type (WT) and Swedish variants (SW) of the βAP sequence (MBP-26) were prepared as standards by the methods described above the MBP-C125 substrates, except that the MPB-26 standards were purified from the lysis buffer in which the *E. coli* had been sonicated. MBP-26 SW standards were used to generate a standard curve (FIG. 8), which allowed the conversion of fluorescent units into amount of product generated.

This assay protocol was used to screen for inhibitor structures, using "libraries" of compounds assembled onto 96-well microtiter plates. Compounds were diluted to a stock concentration of 50 µg/ml in 250 mM sodium acetate, 5% DMSO. Stocks were centrifuged (1,000×g) for five minutes to remove insoluble compounds, and supernatants added to enzyme and substrate mixtures to a final concentration of 20 µl/ml DMSO in the assay format described above. The extent of product generated was compared with control (2% DMSO only) β-secretase incubations, to calculate "% inhibition." "Hits" were defined as compounds which result in >35% inhibition of enzyme activity at test concentration. Using this system, 14 "hits" were identified out of the first 9944 compounds tested, a "hit" rate of 0.14%. Thus, the assay has been shown to be capable of distinguishing "non-inhibitors" (the majority of compounds) from "inhibitors."

Cleavage by β-secretase of the wild-type MBP-C125 wt was measured by the above procedure, with the following modifications: incubation at 37° C. was as above, but in microfuge tubes and for 5 hours. Samples were then diluted 10-fold in Specimen Diluent and transferred to anti-MBP coated plates without further dilution. The reporter antibody was biotinylated wild type specific 192, used at 700 ng/ml. Recombinant wild type MBP-C26 was used to generate a standard curve for conversion of fluorescent units into amount of product (FIG. 9). Varying the amount of β-secretase solution resulted in a corresponding increase in product (FIG. 10), with optimum levels around 6 µl per 50 µl of reaction solution.

2. Assays Utilizing Partially Purified β-Secretase and Synthetic Oliopeptide Substrates β-secretase activity was also measured by incubating the partially purified β-secretase preparations with synthetic oligopeptides comprising the cleavage site in APP. The cleavage products could have been detected by any of several techniques, including but not limited to use of fluorescent or chromogenic tags on the N- or C-termini, measurement of free N- or C-termini, or antibody reaction with the cleaved peptides. In the following example, the cleavage products were detected using high performance liquid chromatography (HPLC). The following peptides were employed:

ADRGL TTRPG SGLTN IKTEE ISEVN LDAEF RHDSG YEVHH QK(26-16'SW) [SEQ ID No.:15]

GSGLT NIKTE EISEV NLDAE FRHDS GYEVH HQK (17-16'SW) [SEQ ID No.:16]

ADRGL TTRPG SGLTN IKTEE ISEVN LDAEF(26-4'SW) [SEQ. ID No.:17]

SEVNL DAEFR HDSGY EVHHQ K(5-16'SW) [SEQ ID No.:18]

N-AcetylSEVNL DAEFR (5-5'SW) [SEQ ID No.:19]

Peptides were prepared by automated solid phase synthesis. The 26-4'SW, 5-16'SW, and 5-5'SW peptides were synthesized with t-BOC chemistry, while the 26-16'SW and 17-16'SW peptides were synthesized by FMOC chemistry. All peptides were purified by reverse-phase HPLC before use, using a 10–50% acetonitrile gradient, at 0.33%/minute, in 0.1% TFA on a C4 column. The peptide substrate was incubated at 0.3–0.35 mg/ml with β-secretase, prepared as described above through the gel exclusion chromatography step. The β-secretase-containing gel exclusion fraction was diluted four-fold in a final assay volume of 250 µl, with a final buffer composition of 100 mM sodium acetate, pH 5.5, and 0.05% reduced Triton X-100. The samples are incubated at 37° C. for overnight (18–20 hours) for peptides 26-16'SW, 26-4'SW, or 17-16'SW, or 70–80 hours for 5-16'SW or 5-5'SW. Following incubation, trifluoroacetic acid was added to a final concentration of 1.0%. The samples were analyzed by HPLC. 26-16'SW, 17-16'SW, or 5-16'SW digests were analyzed on a Vydac C4 column (4.4 mm×250 mm, 300 A pore size, 5µ bead size) using a gradient of 4.5% acetonitrile for 5 minutes, followed by 4.5–22.5% acetonitrile in 40 minutes, 22.5–31.5% in 5 minutes, and 31.5–90% in 10 minutes. 26-4'SW and 5-5'SW digests were analyzed on a Vydac C18 column (4.4 mm×250 mm, 300 A pore size, 5µ bead size) using a gradient of 1.8% acetonitrile for 5 minutes, followed by 1.8–10.8% acetonitrile in 20 minutes, 10.8–18% in 24 minutes, 18–36% in 36 minutes, and 36–90% in 15 minutes. Typical separations of digests of the peptides are shown in FIGS. 11A–11E. Product peptides were identified in selected digests by amino acid analysis and mass spectroscopy. In addition, the C-terminal Leu/Asp cleavage product (DAEFRHDSGYEVHHQK) [SEQ ID No.:20] was confirmed by comparison with the synthetic peptide. Cleavage yields were quantitated by measurement of the intensity or area of the N-terminal (26-4'SW) or C-terminal (all other peptides) product peptide peak. Standard curves using synthetic DAEFRHDSGYEVHHQK [SEQ ID No.:20] showed that the HPLC assay was linear and reproducible (FIG. 11F). When serial gel exclusion fractions from a β-secretase preparation were analyzed by this method, the results were proportional to the β-secretase activity as determined by ELISA (FIGS. 12A–12C), confirming that the same activity is being measured, quantitatively, in both assays. The 17-16'SW peptide is the preferred substrate, since it gave the highest product signal. FIG. 13 shows the results of assays using the 17-16'SW peptide and including two candidate inhibitors (Congo Red and 22408 (FIG. 13A); 22408 was also inactive by the ELISA assay), showing that this assay can be used as an alternate screen for inhibitors, or to verify inhibitors identified in other assays.

3. Assays Utilizing Transfected Cell Membranes

Generation of β-secretase cleaved APP fragments from the endogenous full length APP protein was observed using the 192SW antibody (described above) in membranes from 293 cells transfected with the Swedish variant of APP (293SWE cells). APP fragments may be measured by immunoprecipitation or by immunoblotting. The latter technique is preferred for reasons of convenience. Confirmation that the cleavage activity results from β-secretase was as follows:

1) Both activities were highly selective, generating a single N-terminal product identifiable on immunoblots with the 192SW antibody (see below).
2) Both activities were membrane-bound.
3) The membrane activity was resistant to the standard protease inhibitors listed in Table 3 above.

A semiquantitative assay for the detecting in situ β-secretase cleavage of APP in membranes was developed used to directly identify β-secretase inhibitors. The membrane assay is useful as a primary screen or as a secondary assay to confirm inhibiting activity of potential inhibitors identified in the assays described above.

Cell membrane assays were run as follows. 293SW cells, were grown in medium containing 90% Dulbecco's MEM, 10% heat inactivated fetal bovine serum, 25 mM HEPES, 1 mM pyruvate, 2 mM glutamine, and 0.4 mg/ml geneticin, by standard procedures (see e.g. R. I. Freshney (1987) Animal Cell Culture: A Manual of Basic Technique (2nd Edition) Alan R. Liss, Inc. New York, N.Y.). The cells were harvested by rinsing once with phosphate-buffered saline (PBS), then incubating 5 minutes with PBS containing 2 mM EDTA, with gentle agitation. All further steps were done at 4° C. or on ice, except where noted. Cells were pelleted by centrifugation for 5 minutes at 800×g, then twice resuspended in PBS and repelleted. The cell pellet was homogenized in 5 volumes of homogenization buffer (20 mM HEPES, pH 7.5, 2 mM EDTA, 250 mM sucrose, 1 mM PMSF, 5 µg/ml dichloroisocoumarin, 1 µg/ml pepstatin A, and 5 µg/ml E-64). The homogenate was centrifuged 10 minutes at 800×g. The supernate was saved, while the pellet was resuspended in another 5 volumes of homogenization buffer and recentrifuged. The resulting supernate was pooled with the previous one, aliquoted into 1.0 ml portions, and respun at 16,000×g for 20 minutes. The pellets (P2) were stored at −40° C.

Measurement of in situ β-secretase activity was facilitated by extracting the endogenous β-secretase cleaved APP with saponin. P2 pellets were extracted in 1.0 ml of resuspension buffer (20 mM Tris, pH 7.5, 2 mM EDTA, 1.0 mM PMSF, 5 µg/ml dichloroisocoumarin, 1 µg/ml pepstatin A, and 5 µg/ml E-64) with 0.02% saponin for 30 minutes, pelleted at 16,000×g for 20 minutes, then resuspended by vortexing in the above resuspension buffer, without saponin.

For β-secretase inhibition assays, 10 µl of the test compound of interest at 5 times its desired final concentration, in 500 mM sodium acetate, pH 5.5, and 20% DMSO, was added to 40 µl of the extracted P2 suspension. Samples were incubated at 37C for 4 hours before stopping the reaction with 17 µl of concentrated loading buffer (30% glycerol, 12% sodium dodecyl sulfate, 400 mM Tris, pH 6.7, 40 mM EDTA, 400 mM dithiothreitol, 0.4 mg/ml Bromophenol Blue). Samples were boiled and electrophoresed on 10–20% acrylamide Tricine gels (Novex) and transferred to Immobilon membranes (Millipore). Membranes were blocked in NCS-TBS (10% newborn calf serum, 150 mM sodium chloride, 50 mM Tris, pH 7.5), and analyzed using 192SW, 0.5 µg/ml in NCS-TBS, as primary antibody, horseradish peroxidase-linked anti-rabbit IgG (Amersham) diluted 1:3000 in NCS-TBS as secondary antibody, and ECL reagent (Amersham) as chemilumenescent developer. The 192SW-reactive bands identified by autoradiography were quantitated by densitometry.

As shown in the autoradiograms in FIG. 14, two product bands were identified on immunoblots. The lower and upper bands correspond to cleavage products of the immature, core-glycosylated form and the mature, Golgi-processed, fully glycosylated form of APP, respectively, as shown by their mobilities on electrophoresis and differential sensitivity to neuraminidase and O-glycanase. As shown by the quantitation, normalized to the unincubated, unextracted P2 membranes used as standards (FIG. 15), signal was initially low, and steadily increased with incubation. Further experiments, such as that shown in FIG. 16, showed a slight increase in signal with further incubation.

FIG. 18 shows the concentration dependence of inhibition by three putative inhibitors identified in the ELISA assay. Congo Red and compound 31766 (FIG. 18) were much more potent than an inactive control compound in both the ELISA and the in situ assays.

Although the foregoing invention has been described in some detail by way of illustration and example, for purposes of clarity of understanding, it will be obvious that certain changes and modifications may be practiced within the scope of the appended claims.

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 421 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Ser Lys Asn Lys Val Lys Gly Ser Gln Gly Gln Phe Pro Leu Thr Gln
1               5                   10                  15

Asn Val Thr Val Val Glu Gly Gly Thr Ala Ile Leu Thr Cys Arg Val
```

```
                    20                  25                  30
Asp Gln Asn Asp Asn Thr Ser Leu Gln Trp Ser Asn Pro Ala Gln Gln
                35                  40                  45
Thr Leu Tyr Phe Asp Asp Lys Lys Ala Leu Arg Asp Asn Arg Ile Glu
 50                  55                  60
Leu Val Arg Ala Ser Trp His Glu Leu Ser Ile Ser Val Ser Asp Val
 65                  70                  75                  80
Ser Leu Ser Asp Glu Gly Gln Tyr Thr Cys Ser Leu Phe Thr Met Pro
                85                  90                  95
Val Lys Thr Ser Lys Ala Tyr Leu Thr Val Leu Gly Val Pro Glu Lys
                100                 105                 110
Pro Gln Ile Ser Gly Phe Ser Ser Pro Val Met Glu Gly Asp Leu Met
                115                 120                 125
Gln Leu Thr Cys Lys Thr Ser Gly Ser Lys Pro Ala Ala Asp Ile Arg
                130                 135                 140
Trp Phe Lys Asn Asp Lys Glu Ile Lys Asp Val Lys Tyr Leu Lys Glu
145                 150                 155                 160
Glu Asp Ala Asn Arg Lys Thr Phe Thr Val Ser Ser Thr Leu Asp Phe
                165                 170                 175
Arg Val Asp Arg Ser Asp Asp Gly Val Ala Val Ile Cys Arg Val Asp
                180                 185                 190
His Glu Ser Leu Asn Ala Thr Pro Gln Val Ala Met Gln Val Leu Glu
                195                 200                 205
Ile His Tyr Thr Pro Ser Val Lys Ile Ile Pro Ser Thr Pro Phe Pro
                210                 215                 220
Gln Glu Gly Gln Pro Leu Ile Leu Thr Cys Glu Ser Lys Gly Lys Pro
225                 230                 235                 240
Leu Pro Glu Pro Val Leu Trp Thr Lys Asp Gly Gly Glu Leu Pro Asp
                245                 250                 255
Pro Asp Arg Met Val Val Ser Gly Arg Glu Leu Asn Ile Leu Phe Leu
                260                 265                 270
Asn Lys Thr Asp Asn Gly Thr Tyr Arg Cys Glu Ala Thr Asn Thr Ile
                275                 280                 285
Gly Gln Ser Ser Ala Glu Tyr Val Leu Ile Val His Asp Val Pro Asn
                290                 295                 300
Thr Leu Leu Pro Thr Thr Ile Ile Pro Ser Leu Thr Thr Ala Thr Val
305                 310                 315                 320
Thr Thr Thr Val Ala Ile Thr Thr Ser Pro Thr Thr Ser Ala Thr Thr
                325                 330                 335
Ser Ser Ile Arg Asp Pro Asn Ala Leu Ala Gly Gln Asn Gly Pro Asp
                340                 345                 350
His Ala Leu Ile Gly Gly Ile Val Ala Val Val Phe Val Thr Leu
                355                 360                 365
Cys Ser Ile Phe Leu Leu Gly Arg Tyr Leu Ala Arg His Lys Gly Thr
                370                 375                 380
Tyr Leu Thr Asn Glu Ala Lys Gly Ala Glu Asp Ala Pro Asp Ala Asp
385                 390                 395                 400
Thr Ala Ile Ile Asn Ala Glu Gly Ser Gln Val Asn Ala Glu Glu Lys
                405                 410                 415
Lys Glu Tyr Phe Ile
                420

(2) INFORMATION FOR SEQ ID NO:2:
```

(i) SEQUENCE CHARACTERISTICS:
    (A) LENGTH: 1266 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:2:

| | | | | | |
|---|---|---|---|---|---|
| TCAAAGAATA | AAGTTAAAGG | CAGCCAAGGG | CAGTTTCCAC | TAACACAGAA | TGTAACCGTT | 60 |
| GTTGAAGGTG | GAACTGCAAT | TTTGACCTGC | AGGGTTGATC | AAAATGATAA | CACCTCCCTC | 120 |
| CAGTGGTCAA | ATCCAGCTCA | ACAGACTCTG | TACTTTGACG | ACAAGAAAGC | TTTAAGGGAC | 180 |
| AATAGGATCG | AGCTGGTTCG | CGCTTCCTGG | CATGAATTGA | GTATTAGTGT | CAGTGATGTG | 240 |
| TCTCTCTCTG | ATGAAGGACA | GTACACCTGT | TCTTTATTTA | CAATGCCTGT | CAAAACTTCC | 300 |
| AAGGCATATC | TCACCGTTCT | GGGTGTTCCT | GAAAAGCCTC | AGATTAGTGG | ATTCTCATCA | 360 |
| CCAGTTATGG | AGGGTGACTT | GATGCAGCTG | ACTTGCAAAA | CATCTGGTAG | TAAACCTGCA | 420 |
| GCTGATATAA | GATGGTTCAA | AAATGACAAA | GAGATTAAAG | ATGTAAAATA | TTTAAAAGAA | 480 |
| GAGGATGCAA | ATCGCAAGAC | ATTCACTGTC | AGCAGCACAC | TGGACTTCCG | AGTGGACCGG | 540 |
| AGTGATGATG | GAGTGGCGGT | CATCTGCAGA | GTAGATCACG | AATCCCTCAA | TGCCACCCCT | 600 |
| CAGGTAGCCA | TGCAGGTGCT | AGAAATACAC | TATACACCAT | CAGTTAAGAT | TATACCATCG | 660 |
| ACTCCTTTTC | CACAAGAAGG | ACAGCCTTTA | ATTTTGACTT | GTGAATCCAA | AGGAAAACCA | 720 |
| CTGCCAGAAC | CTGTTTTGTG | GACAAAGGAT | GGCGGAGAAT | TACCAGATCC | TGACCGAATG | 780 |
| GTTGTGAGTG | GTAGGGAGCT | AAACATTCTT | TTCCTGAACA | AAACGGATAA | TGGTACATAT | 840 |
| CGATGTGAAG | CCACAAACAC | CATTGGCCAA | AGCAGTGCGG | AATATGTTCT | CATTGTGCAT | 900 |
| GATGTTCCCA | ACACTTTGCT | TCCCACTACT | ATCATCCCCT | CCCTTACCAC | TGCAACAGTC | 960 |
| ACAACCACTG | TAGCCATAAC | AACCAGCCCA | ACCACATCTG | CAACAACCAG | CAGCATCAGA | 1020 |
| GATCCTAATG | CTTTGGCTGG | CCAGAATGGC | CCTGACCATG | CTCTCATAGG | AGGAATAGTG | 1080 |
| GCTGTAGTTG | TATTTGTCAC | GCTGTGTTCT | ATCTTTCTGC | TTGGTCGATA | TCTGGCAAGG | 1140 |
| CATAAAGGAA | CGTATTTAAC | AAATGAAGCT | AAAGGAGCTG | AAGATGCACC | AGATGCTGAT | 1200 |
| ACAGCCATTA | TCAATGCTGA | AGGCAGCCAA | GTCAATGCTG | AAGAGAAAAA | AGAGTATTTC | 1260 |
| ATTTAA | | | | | | 1266 |

(2) INFORMATION FOR SEQ ID NO:3:

(i) SEQUENCE CHARACTERISTICS:
        (A) LENGTH: 1521 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

| | | | | | |
|---|---|---|---|---|---|
| ATGAAAACTG | AAGAAGGTAA | ACTGGTAATC | TGGATTAACG | GCGATAAAGG | CTATAACGGT | 60 |
| CTCGCTGAAG | TCGGTAAGAA | ATTCGAGAAA | GATACCGGAA | TTAAAGTCAC | CGTTGAGCAT | 120 |
| CCGGATAAAC | TGGAAGAGAA | ATTCCCACAG | GTTGCGGCAA | CTGGCGATGG | CCCTGACATT | 180 |
| ATCTTCTGGG | CACACGACCG | CTTTGGTGGC | TACGCTCAAT | CTGGCCTGTT | GGCTGAAATC | 240 |
| ACCCCGGACA | AAGCGTTCCA | GGACAAGCTG | TATCCGTTTA | CCTGGGATGC | CGTACGTTAC | 300 |
| AACGGCAAGC | TGATTGCTTA | CCCGATCGCT | GTTGAAGCGT | TATCGCTGAT | TTATAACAAA | 360 |

-continued

```
GATCTGCTGC CGAACCCGCC AAAAACCTGG GAAGAGATCC CGGCGCTGGA TAAAGAACTG        420

AAAGCGAAAG GTAAGAGCGC GCTGATGTTC AACCTGCAAG AACCGTACTT CACCTGGCCG        480

CTGATTGCTG CTGACGGGGG TTATGCGTTC AAGTATGAAA ACGGCAAGTA CGACATTAAA        540

GACGTGGGCG TGGATAACGC TGGCGCGAAA GCGGGTCTGA CCTTCCTGGT TGACCTGATT        600

AAAAACAAAC ACATGAATGC AGACACCGAT TACTCCATCG CAGAAGCTGC CTTTAATAAA        660

GGCGAAACAG CGATGACCAT CAACGGCCCG TGGGCATGGT CCAACATCGA CACCAGCAAA        720

GTGAATTATG GTGTAACGGT ACTGCCGACC TTCAAGGGTC AACCATCCAA ACCGTTCGTT        780

GGCGTGCTGA GCGCAGGTAT TAACGCCGCC AGTCCGAACA AAGAGCTGGC GAAAGAGTTC        840

CTCGAAAACT ATCTGCTGAC TGATGAAGGT CTGGAAGCGG TTAATAAAGA CAAACCGCTG        900

GGTGCCGTAG CGCTGAAGTC TTACGAGGAA GAGTTGGCGA AGATCCACG TATTGCCGCC        960

ACCATGGAAA ACGCCCAGAA AGGTGAAATC ATGCCGAACA TCCCGCAGAT GTCCGCTTTC       1020

TGGTATGCCG TGCGTACTGC GGTGATCAAC GCCGCCAGCG GTCGTCAGAC TGTCGATGAA       1080

GCCCTGAAAG ACGCGCAGAC TAATTCGAGC TCGGTACCCG GCCGGGGATC CATCGAGGGT       1140

AGGGCCGACC GAGGACTGAC CACTCGACCA GGTTCTGGGT TGACAAATAT CAAGACGGAG       1200

GAGATCTCTG AAGTGAATCT GGATGCAGAA TTCCGACATG ACTCAGGATA TGAAGTTCAT       1260

CATCAAAAAT TGGTGTTCTT TGCAGAAGAT GTGGGTTCAA ACAAAGGTGC AATCATTGGA       1320

CTCATGGTGG GCGGTGTTGT CATAGCGACA GTGATCGTCA TCACCTTGGT GATGCTGAAG       1380

AAGAAACAGT ACACATCCAT TCATCATGGT GTGGTGGAGG TTGACGCCGC TGTCACCCCA       1440

GAGGAGCGCC ACCTGTCCAA GATGCAGCAG AACGGCTACG AAAATCCAAC CTACAAGTTC       1500

TTTGAGCAGA TGCAGAACTA G                                                 1521
```

(2) INFORMATION FOR SEQ ID NO:4:

(i) SEQUENCE CHARACTERISTICS:
        (A) LENGTH: 1335 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
ATGATTTGGA AACGCAGCGC CGTTCTCCGC TTCTACAGTG TCTGCGGGCT CCTGCTACAA         60

GCGGCTGCTT CAAAGAATAA AGTTAAAGGC AGCCAAGGGC AGTTCCACT AACACAGAAT        120

GTAACCGTTG TTGAAGGTGG AACTGCAATT TTGACCTGCA GGGTTGATCA AAATGATAAC        180

ACCTCCCTCC AGTGGTCAAA TCCAGCTCAA CAGACTCTGT ACTTTGACGA CAAGAAAGCT        240

TTAAGGGACA ATAGGATCGA GCTGGTTCGC GCTTCCTGGC ATGAATTGAG TATTAGTGTC        300

AGTGATGTGT CTCTCTCTGA TGAAGGACAG TACACCTGTT CTTTATTTAC AATGCCTGTC        360

AAAACTTCCA AGGCATATCT CACCGTTCTG GGTGTTCCTG AAAAGCCTCA GATTAGTGGA        420

TTCTCATCAC CAGTTATGGA GGGTGACTTG ATGCAGCTGA CTTGCAAAAC ATCTGGTAGT        480

AAACCTGCAG CTGATATAAG ATGGTTCAAA AATGACAAAG AGATTAAAGA TGTAAAATAT        540

TTAAAAGAAG AGGATGCAAA TCGCAAGACA TTCACTGTCA GCAGCACACT GGACTTCCGA        600

GTGGACCGGA GTGATGATGG AGTGGCGGTC ATCTGCAGAG TAGATCACGA ATCCCTCAAT        660

GCCACCCCTC AGGTAGCCAT GCAGGTGCTA GAAATACACT ATACACCATC AGTTAAGATT        720

ATACCATCGA CTCCTTTTCC ACAAGAAGGA CAGCCTTTAA TTTTGACTTG TGAATCCAAA        780
```

```
GGAAAACCAC TGCCAGAACC TGTTTTGTGG ACAAAGGATG GCGGAGAATT ACCAGATCCT      840

GACCGAATGG TTGTGAGTGG TAGGGAGCTA AACATTCTTT TCCTGAACAA ACGGATAAT       900

GGTACATATC GATGTGAAGC CACAAACACC ATTGGCCAAA GCAGTGCGGA ATATGTTCTC      960

ATTGTGCATG ATGTTCCCAA CACTTTGCTT CCCACTACTA TCATCCCCTC CCTTACCACT     1020

GCAACAGTCA CAACCACTGT AGCCATAACA CCAGCCCAA CCACATCTGC AACAACCAGC     1080

AGCATCAGAG ATCCTAATGC TTTGGCTGGC CAGAATGGCC CTGACCATGC TCTCATAGGA     1140

GGAATAGTGG CTGTAGTTGT ATTTGTCACG CTGTGTTCTA TCTTTCTGCT TGGTCGATAT     1200

CTGGCAAGGC ATAAAGGAAC GTATTTAACA AATGAAGCTA AAGGAGCTGA AGATGCACCA     1260

GATGCTGATA CAGCCATTAT CAATGCTGAA GGCAGCCAAG TCAATGCTGA AGAGAAAAAA     1320

GAGTATTTCA TTTAA                                                      1335
```

(2) INFORMATION FOR SEQ ID NO:5:

(i) SEQUENCE CHARACTERISTICS:
        (A) LENGTH: 444 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Ile Trp Lys Arg Ser Ala Val Leu Arg Phe Tyr Ser Val Cys Gly
1               5                   10                  15

Leu Leu Leu Gln Ala Ala Ala Ser Lys Asn Lys Val Lys Gly Ser Gln
            20                  25                  30

Gly Gln Phe Pro Leu Thr Gln Asn Val Thr Val Glu Gly Gly Thr
        35                  40                  45

Ala Ile Leu Thr Cys Arg Val Asp Gln Asn Asp Thr Ser Leu Gln
    50                  55                  60

Trp Ser Asn Pro Ala Gln Gln Thr Leu Tyr Phe Asp Asp Lys Lys Ala
65                  70                  75                  80

Leu Arg Asp Asn Arg Ile Glu Leu Val Arg Ala Ser Trp His Glu Leu
                85                  90                  95

Ser Ile Ser Val Ser Asp Val Ser Leu Ser Asp Glu Gly Gln Tyr Thr
            100                 105                 110

Cys Ser Leu Phe Thr Met Pro Val Lys Thr Ser Lys Ala Tyr Leu Thr
        115                 120                 125

Val Leu Gly Val Pro Glu Lys Pro Gln Ile Ser Gly Phe Ser Ser Pro
    130                 135                 140

Val Met Glu Gly Asp Leu Met Gln Leu Thr Cys Lys Thr Ser Gly Ser
145                 150                 155                 160

Lys Pro Ala Ala Asp Ile Arg Trp Phe Lys Asn Asp Lys Glu Ile Lys
                165                 170                 175

Asp Val Lys Tyr Leu Lys Glu Gly Asp Ala Asn Arg Lys Thr Phe Thr
            180                 185                 190

Val Ser Ser Thr Leu Asp Phe Arg Val Asp Arg Ser Asp Asp Gly Val
        195                 200                 205

Ala Val Ile Cys Arg Val Asp His Glu Ser Leu Asn Ala Thr Pro Gln
    210                 215                 220

Val Ala Met Gln Val Leu Glu Ile His Tyr Thr Pro Ser Val Lys Ile
225                 230                 235                 240
```

```
Ile Pro Ser Thr Pro Phe Pro Gln Glu Gly Gln Pro Leu Ile Leu Thr
                245                 250                 255
Cys Glu Ser Lys Gly Lys Pro Leu Pro Glu Pro Val Leu Trp Thr Lys
                260                 265                 270
Asp Gly Gly Glu Leu Pro Asp Pro Asp Arg Met Val Val Ser Gly Arg
                275                 280                 285
Glu Leu Asn Ile Leu Phe Leu Asn Lys Thr Asp Asn Gly Thr Tyr Arg
                290                 295                 300
Cys Glu Ala Thr Asn Thr Ile Gly Gln Ser Ser Ala Glu Tyr Val Leu
305                 310                 315                 320
Ile Val His Asp Val Pro Asn Thr Leu Leu Pro Thr Thr Ile Ile Pro
                325                 330                 335
Ser Leu Thr Thr Ala Thr Val Thr Thr Val Ala Ile Thr Thr Ser
                340                 345                 350
Pro Thr Thr Ser Ala Thr Thr Ser Ser Ile Arg Asp Pro Asn Ala Leu
                355                 360                 365
Ala Gly Gln Asn Gly Pro Asp His Ala Leu Ile Gly Gly Ile Val Ala
                370                 375                 380
Val Val Val Phe Val Thr Leu Cys Ser Ile Phe Leu Leu Gly Arg Tyr
385                 390                 395                 400
Leu Ala Arg His Lys Gly Thr Tyr Leu Thr Asn Glu Ala Lys Gly Ala
                405                 410                 415
Glu Asp Ala Pro Asp Ala Asp Thr Ala Ile Ile Asn Ala Glu Gly Ser
                420                 425                 430
Gln Val Asn Ala Glu Glu Lys Lys Glu Tyr Phe Ile
                435                 440

(2) INFORMATION FOR SEQ ID NO:6:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Ala Tyr Leu Thr Val Leu Gly Val Pro Glu Lys Pro Gln Ile Ser Gly
1               5                   10                  15
Phe Ser Arg (2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ile Ile Pro Ser Thr Pro Phe Pro Gln Glu Cys Gln Pro Leu Ile Leu
1               5                   10                  15
Thr Cys Glu Arg
                20

(2) INFORMATION FOR SEQ ID NO:8:
```

```
    (i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Gly Lys Pro Leu Pro Glu Pro Val Leu Trp Thr Lys
1               5                   10

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(15)
        (D) OTHER INFORMATION: /note= "C-terminal Gln is
            amidated."

(xi) SEQUENCE DESCRIPTION: SEQ ID NO:9:

Cys Gly Gly Tyr Leu Thr Val Leu Gly Val Pro Glu Lys Gln Pro
1               5                   10                  15

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(1)
        (D) OTHER INFORMATION: /note= "N-terminal Asn is
            acetylated."

(xi) SEQUENCE DESCRIPTION: SEQ ID NO:10:

Asn His Ile Ile Pro Ser Thr Pro Phe Pro Gln Glu Gly Gln Pro Leu
1               5                   10                  15

Ile Leu Thr Cys
        20

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(14)
        (D) OTHER INFORMATION: /note= "C-terminal Lys is
            amidated."

(xi) SEQUENCE DESCRIPTION: SEQ ID NO:11:
```

```
Cys Gly Gly Lys Pro Leu Pro Glu Pro Val Leu Trp Thr Lys
1               5                   10
```

(2) INFORMATION FOR SEQ ID NO:12:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(1)
        (D) OTHER INFORMATION: /note= "Xaa is Ser, Phe or Gly."

(xi) SEQUENCE DESCRIPTION: SEQ ID NO:12:

```
Xaa Lys Asn Lys Val Lys Gly Ser Gln Gly Gln Phe Pro Leu Thr Gln
1               5                   10                  15

Xaa Val Thr Val Val
```

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Val Lys Met Asp Ala
1               5
```

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Val Asn Leu Asp Ala
1               5
```

(2) INFORMATION FOR SEQ ID NO:15:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe Arg His
                20                  25                  30

Asp Ser Gly Tyr Glu Val His His Gln Lys
                35                  40
```

(2) INFORMATION FOR SEQ ID NO:16:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Gly Ser Gly Leu Thr Asn Ile Lys Thr Glu Glu Ile Ser Glu Val Asn
1               5                   10                  15
Leu Asp Ala Glu Phe Arg His Asp Ser Gly Tyr Glu Val His His Gln
            20                  25                  30
Lys
```

(2) INFORMATION FOR SEQ ID NO:17:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Ala Asp Arg Gly Leu Thr Thr Arg Pro Gly Ser Gly Leu Thr Asn Ile
1               5                   10                  15
Lys Thr Glu Glu Ile Ser Glu Val Asn Leu Asp Ala Glu Phe
            20                  25                  30
```

(2) INFORMATION FOR SEQ ID NO:18:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Ser Glu Val Asn Leu Asp Ala Glu Phe Arg His Asp Ser Gly Tyr Glu
1               5                   10                  15
Val His His Gln Lys
            20
```

(2) INFORMATION FOR SEQ ID NO:19:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(1)
        (D) OTHER INFORMATION: /note= "N-terminal Ser is acetylated."

(xi) SEQUENCE DESCRIPTION: SEQ ID NO:19:

```
Ser Glu Val Asn Leu Asp Ala Glu Phe Arg
```

1            5                    10

(2) INFORMATION FOR SEQ ID NO:20:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Asp Ala Glu Phe Arg His Asp Ser Gln Tyr Glu Val His His Gln Lys
1               5                   10                  15

(2) INFORMATION FOR SEQ ID NO:21:

(i) SEQUENCE CHARACTERISTICS:
        (A) LENGTH: 506 amino acids
        (B) TYPE: amino acid
        (D) TOPOLOGY: linear (ii) MOLECULE TYPE: protein (xi) SEQUENCE DESCRIPTION: SEQ ID NO:21:

Met Lys Thr Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro

-continued

```
                    260                 265                 270
Asn Lys Glu Leu Ala Lys Glu Phe Leu Glu Asn Tyr Leu Leu Thr Asp
        275                 280                 285
Glu Gly Leu Glu Ala Val Asn Lys Asp Lys Pro Leu Gly Ala Val Ala
        290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
                340                 345                 350
Ser Gly Arg Gln Thr Val Asp Glu Ala Leu Lys Asp Ala Gln Thr Asn
        355                 360                 365
Ser Ser Ser Val Pro Gly Arg Gly Ser Ile Glu Gly Arg Ala Asp Arg
        370                 375                 380
Gly Leu Thr Thr Arg Pro Gly Ser Gly Leu Thr Asn Ile Lys Thr Glu
385                 390                 395                 400
Glu Ile Ser Glu Val Asn Leu Asp Ala Glu Phe Arg His Asp Ser Gly
                405                 410                 415
Tyr Glu Val His His Gln Lys Leu Val Phe Phe Ala Glu Asp Val Gly
                420                 425                 430
Ser Asn Lys Gly Ala Ile Ile Gly Leu Met Val Gly Gly Val Val Ile
            435                 440                 445
Ala Thr Val Ile Val Ile Thr Leu Val Met Leu Lys Lys Lys Gln Tyr
        450                 455                 460
Thr Ser Ile His His Gly Val Val Glu Val Asp Ala Ala Val Thr Pro
465                 470                 475                 480
Glu Glu Arg His Leu Ser Lys Met Gln Gln Asn Gly Tyr Glu Asn Pro
                485                 490                 495
Thr Tyr Lys Phe Phe Glu Gln Met Gln Asn
                500                 505
```

What is claimed is:

1. An antibody that specifically binds a native β-secretase protein characterized by:
   an ability to cleave the 695-amino acid isotype of β-amyloid precursor protein between amino acids 596 and 597; and
   an apparent molecular weight in the range from 260 kD to 300 kD when measured by gel exclusion chromatography.

2. The antibody of claim 1 that is a polyclonal antibody.

3. The antibody of claim 1 that is a monoclonal antibody.

4. The antibody of claim 1 that is a humanized antibody.

5. The antibody of claim 1 that is an antibody fragment.

* * * * *